(12) United States Patent
Kälvesten et al.

(10) Patent No.: US 8,637,351 B2
(45) Date of Patent: Jan. 28, 2014

(54) METHODS FOR MAKING MICRO NEEDLES AND APPLICATIONS THEREOF

(75) Inventors: Edvard Kälvesten, Hägersten (SE); Thorbjörn Ebefors, Huddinge (SE); Thierry Corman, Sollentuna (SE)

(73) Assignee: Silex Microsystem AB, Jarfalla (SE)

( * ) Notice: Subject to any disclaimer, the term of this patent is extended or adjusted under 35 U.S.C. 154(b) by 0 days.

(21) Appl. No.: 13/278,890

(22) Filed: Oct. 21, 2011

(65) Prior Publication Data

US 2012/0126392 A1    May 24, 2012

Related U.S. Application Data

(63) Continuation of application No. 12/097,448, filed as application No. PCT/SE2006/050582 on Dec. 14, 2006, now Pat. No. 8,308,960.

(60) Provisional application No. 60/750,047, filed on Dec. 14, 2005.

(30) Foreign Application Priority Data

Dec. 14, 2005  (SE) ..................................... 0502760

(51) Int. Cl.
  *H01L 21/00*   (2006.01)
(52) U.S. Cl.
  USPC .................... 438/113; 257/774; 257/E21.599

(58) Field of Classification Search
  USPC .......................... 438/113; 257/E21.599, 774
  See application file for complete search history.

(56) References Cited

U.S. PATENT DOCUMENTS

| | | |
|---|---|---|
| 4,585,991 A | 4/1986 | Reid et al. |
| 2001/0054771 A1 | 12/2001 | Wark et al. |
| 2003/0173678 A1* | 9/2003 | Mizukoshi .................... 257/774 |
| 2005/0261632 A1 | 11/2005 | Xu |

FOREIGN PATENT DOCUMENTS

| | | |
|---|---|---|
| WO | 0133614 A1 | 5/2001 |
| WO | 0152731 A1 | 7/2001 |
| WO | 03015860 A1 | 2/2003 |

* cited by examiner

*Primary Examiner* — Duy Deo
*Assistant Examiner* — Mahmoud Dahimene
(74) *Attorney, Agent, or Firm* — Pierce Atwood LLP; Kevin M. Farrell

(57) ABSTRACT

The invention relates in a general aspect to a method of making vertically protruding elements on a substrate, said elements having a tip comprising at least one inclined surface and an elongated body portion extending between said substrate and said tip. The method comprises an anisotropic, crystal plane dependent etch forming said inclined surface(s); and an anisotropic, non crystal plane dependent etch forming said elongated body portion; combined with suitable patterning processes defining said protruding elements to have a predetermined base geometry.

6 Claims, 35 Drawing Sheets

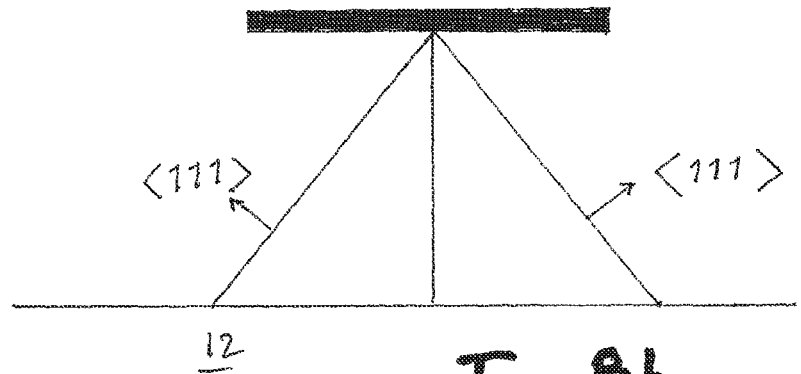
Fig. 8b
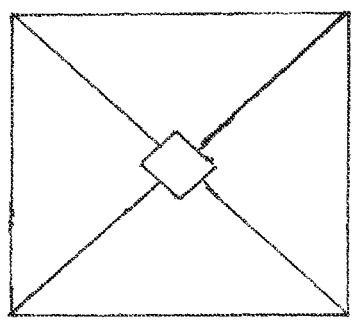
Fig. 8c
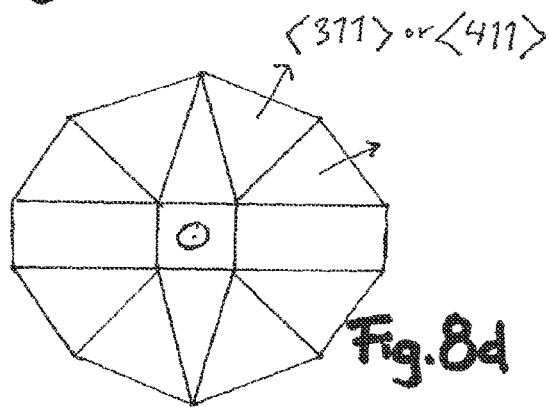
Fig. 8d
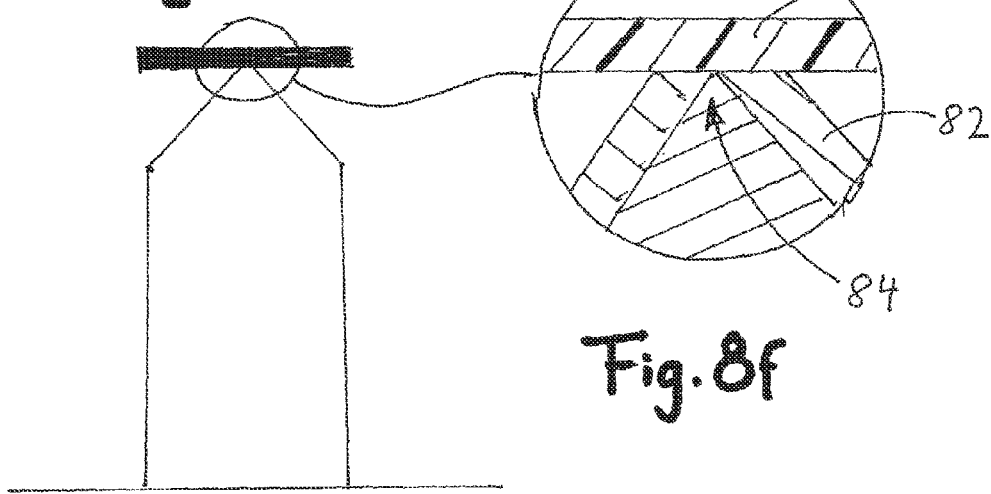
Fig. 8e
Fig. 8f

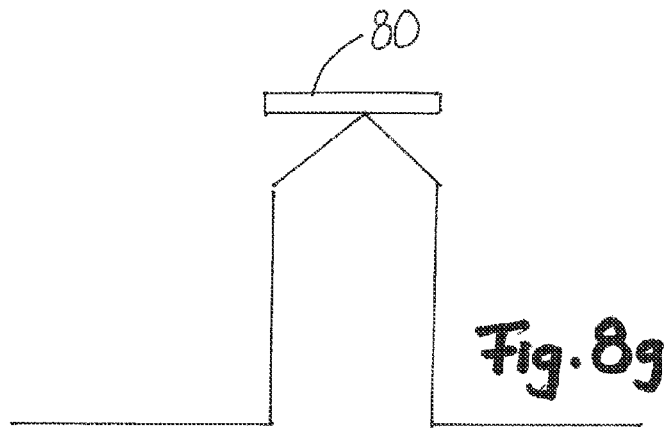
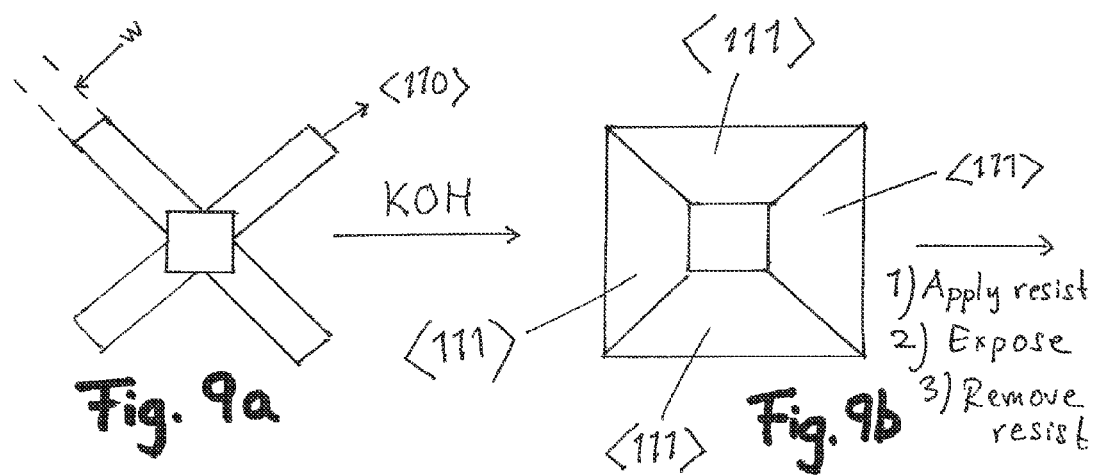

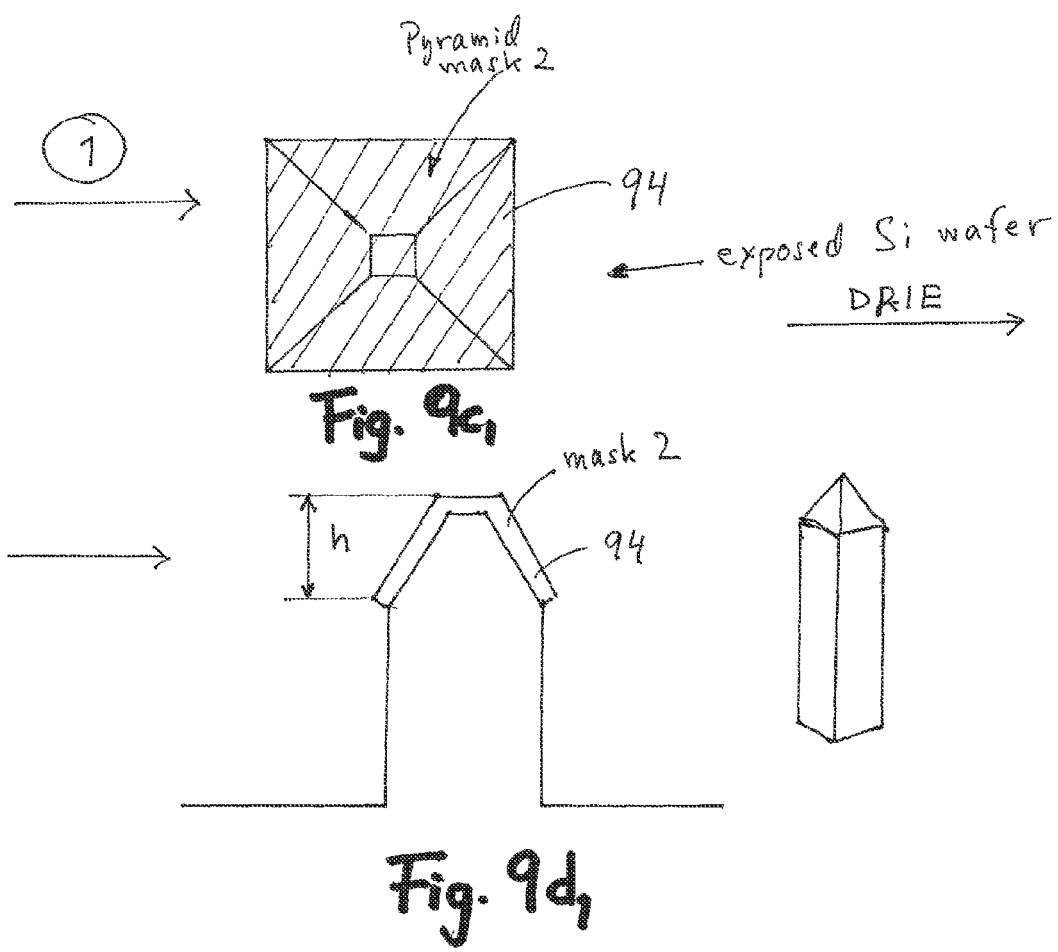

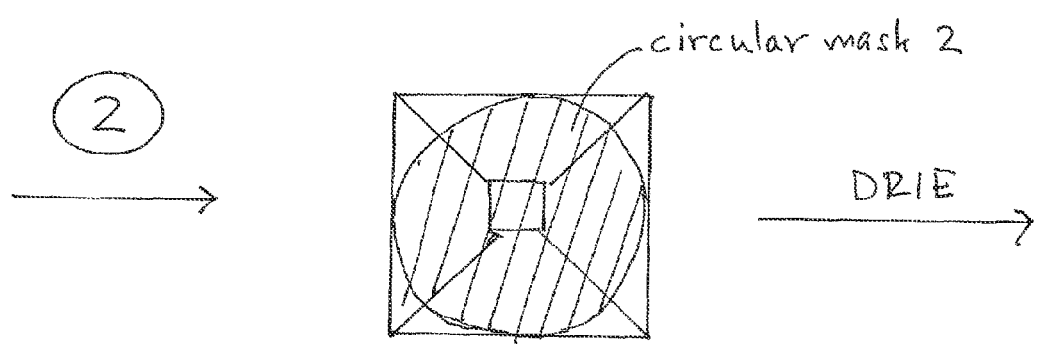
Fig. 9c₂
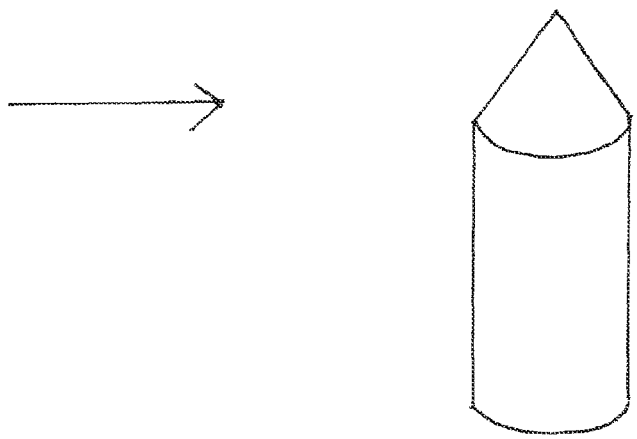
Fig. 9d₂

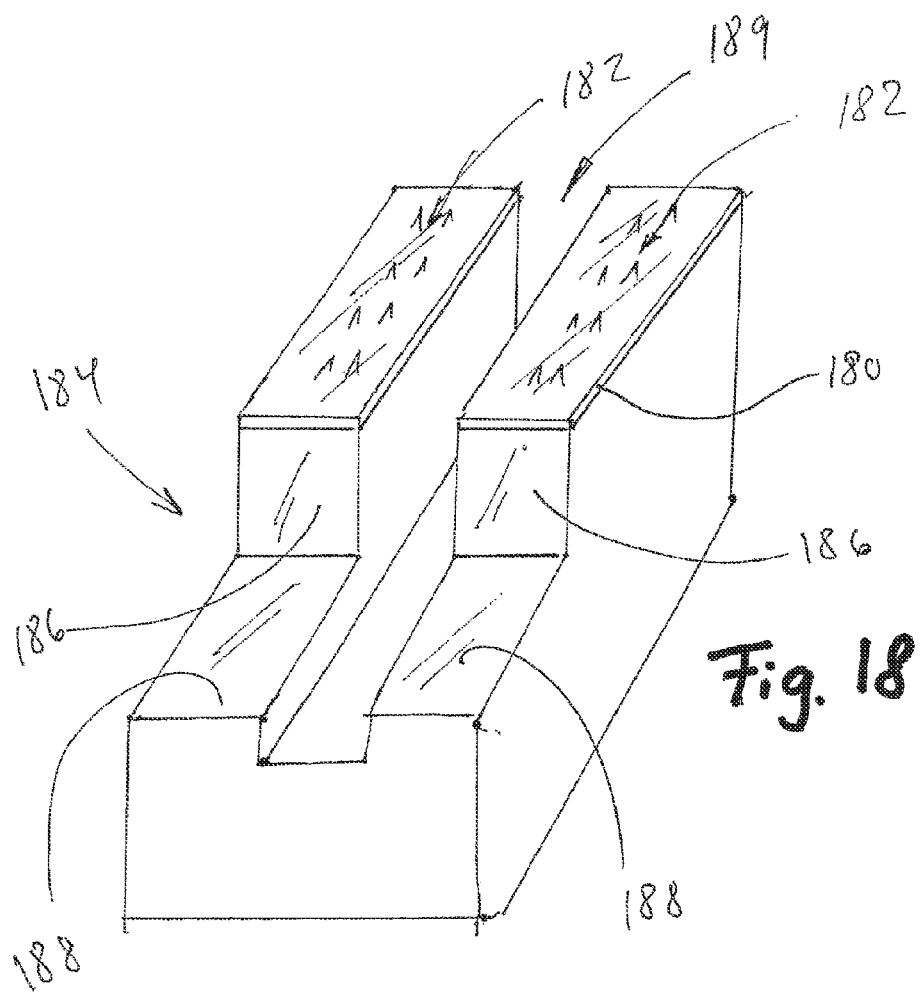

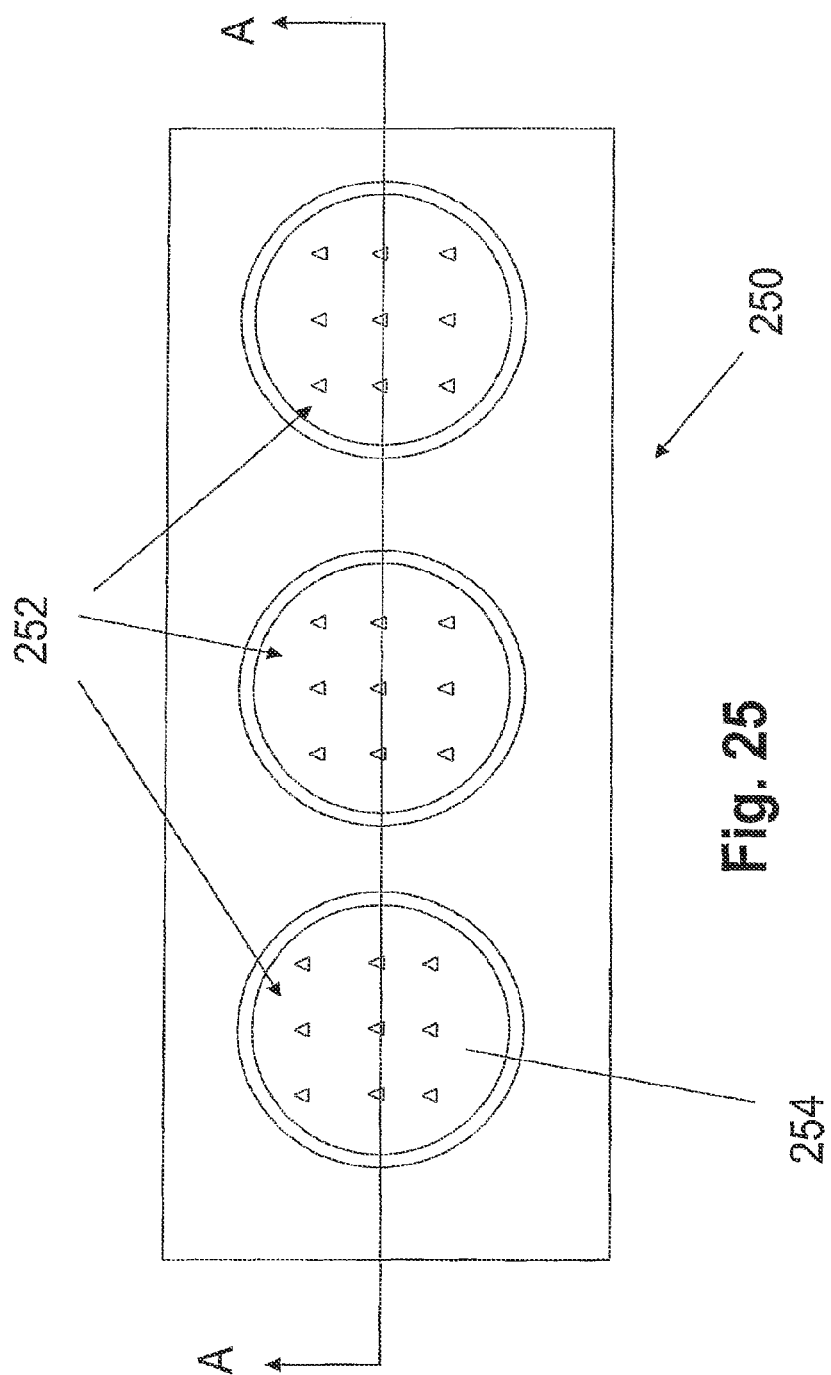

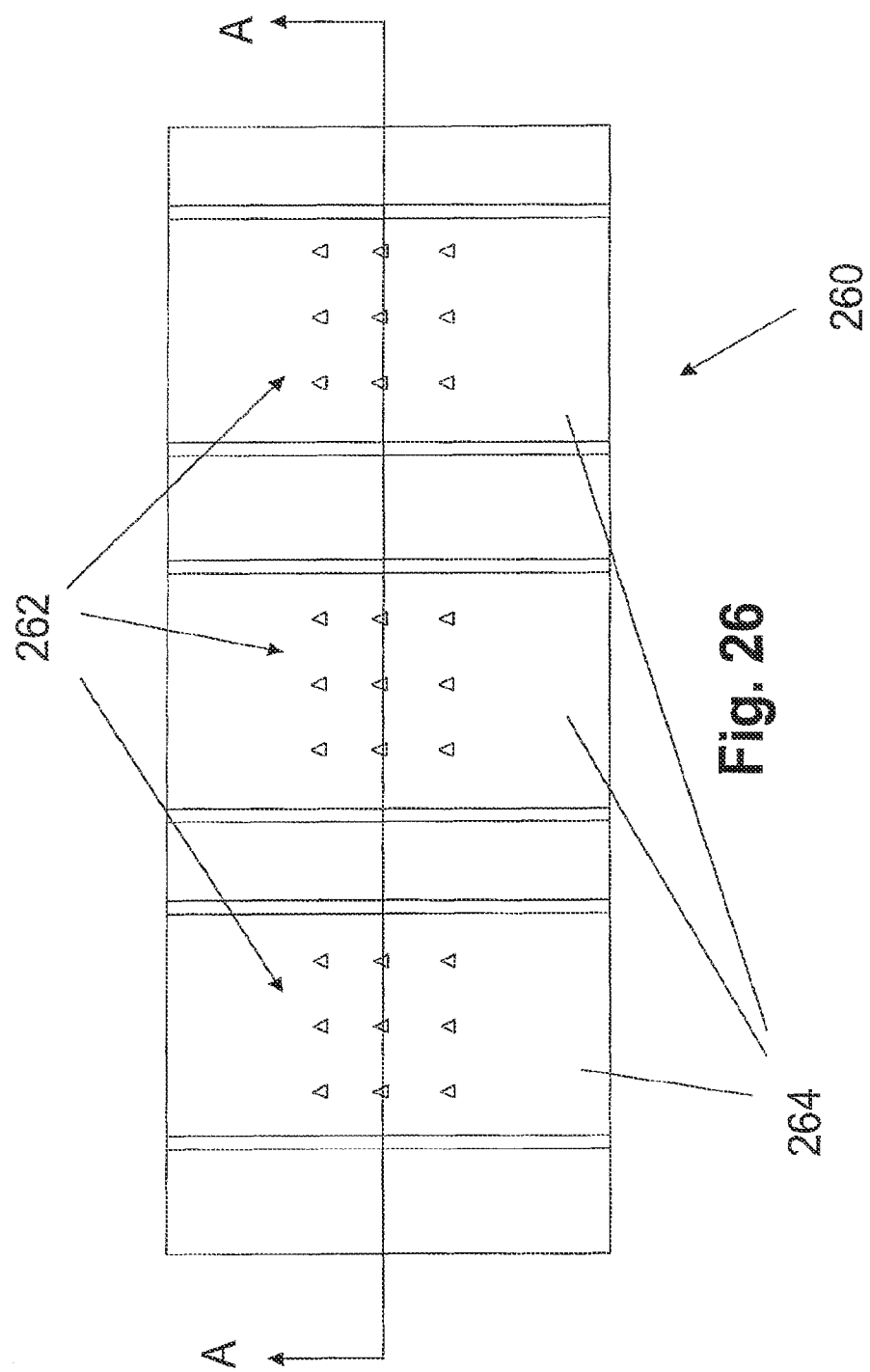

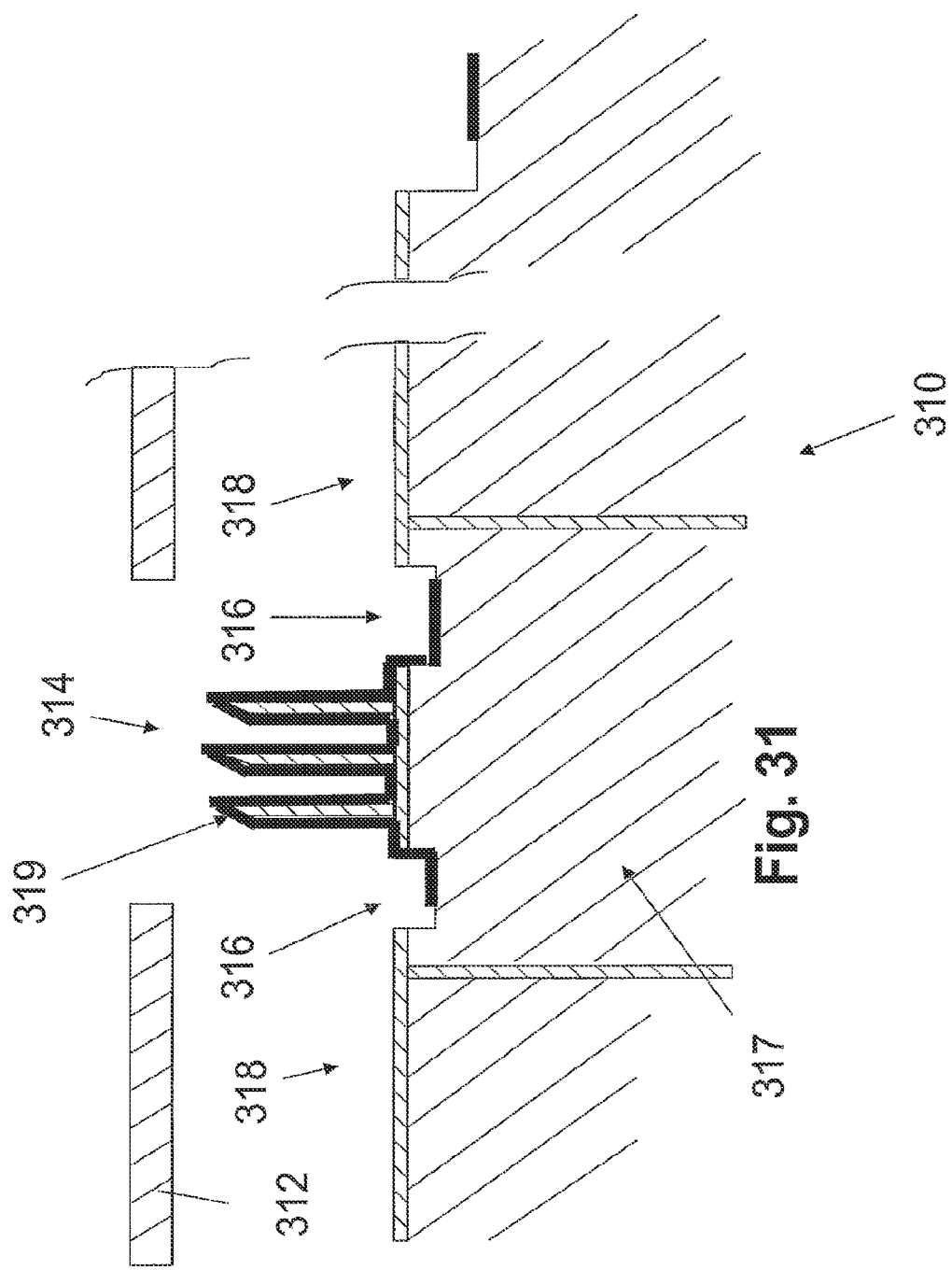

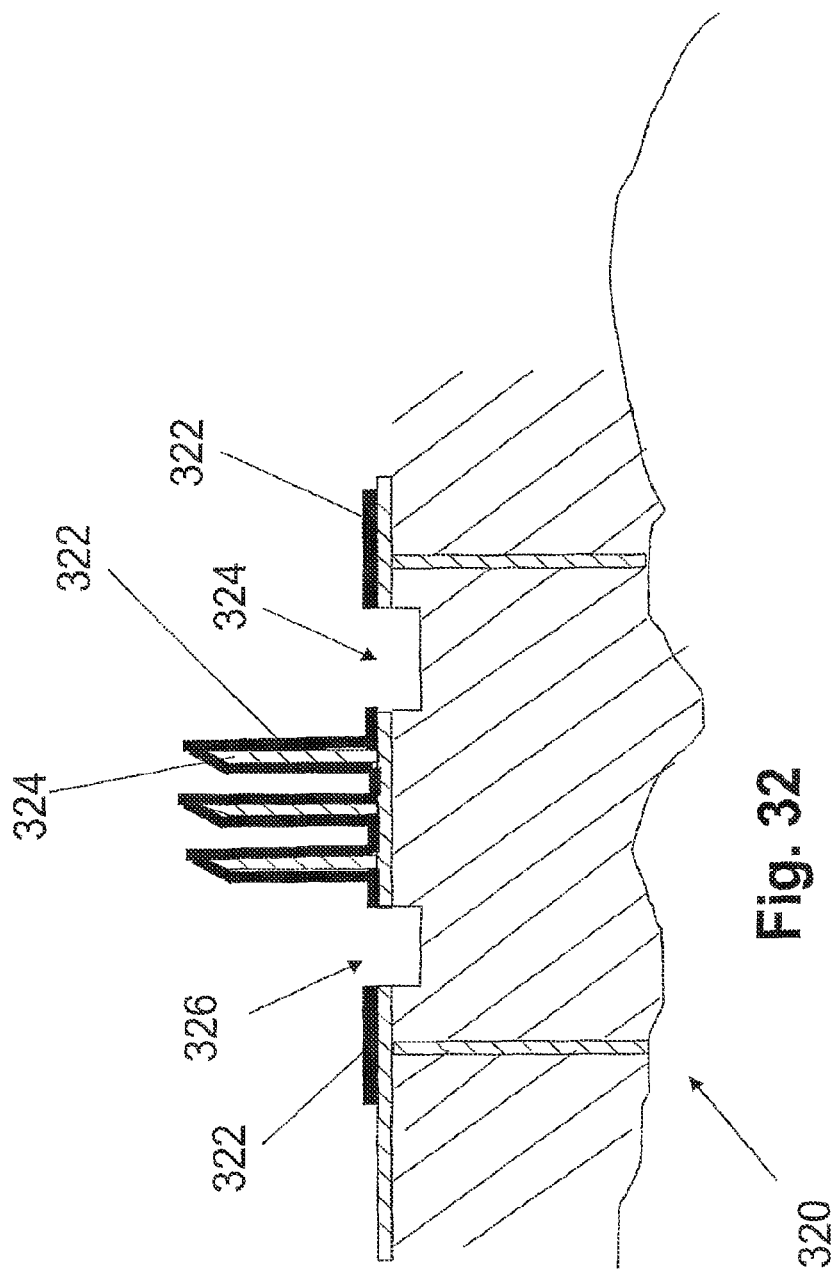

METHODS FOR MAKING MICRO NEEDLES AND APPLICATIONS THEREOF

CROSS-REFERENCE TO RELATED APPLICATION

This application claims priority to and is a continuation of U.S. application Ser. No. 12/097,448 filed under 35 USC 371 on Jun. 13, 2008 as a U.S. National Stage Application of PCT Application No. PCT/SE06/50582 filed on Dec. 14, 2006, which claims priority to U.S. Provisional Application No. 60/750,047 filed on Dec. 14, 2005 and Swedish Application No. 0502760-2 filed on Dec. 14, 2005, the entire contents of which are herein incorporated by reference as part of this application.

FIELD OF THE INVENTION

The present invention relates to methods for making needles in the micrometer scale. In particular it relates to the manufacture of needles having a tip resembling a cannula type of tip, i.e. with an inclined tip portion.

BACKGROUND OF THE INVENTION

Micro-sized needles, i.e. needles having diameters and lengths in the micrometer range, find great utility i.a. in many medical applications. As an example, injection of liquid such as drugs of various kinds, vaccines etc. through the skin is often performed. However, when ordinary syringes are used for the administration it can sometimes cause pain or discomfort to a patient.

Micro-needles can be used in such applications to reduce the pain experienced by the patient. In particular arrays of hollow micro-needles provided on a patch that is applied to the skin and through which medicaments are administered will reduce the pain and discomfort substantially.

Other fields of application are various electrical measurements performed on the skin, using arrays of micro-needles.

There are several patents granted for methods of making micro needles, a few of which are recited below.

US published patent application 2004/0054393 (corresponding to EP 1 164 928) (Stemme et al) discloses a medical electrode for obtaining biopotentials from the skin of a subject or electrically stimulating the subject's skin and deeper tissue layers. The electrode has a carrier base member from which project a plurality of spikes arranged in an array on one surface of the base member. The spikes are sufficiently long to penetrate through the stratum corneum into the stratum germinativum of the subject's skin. The spikes may be formed by a deep reactive ion etching process on a silicon wafer forming the base member. A fluid container may be formed on another surface of the skin for providing a drug to the surface of the skin through holes in the base member. The action of the spikes on the skin enhances administration of the drug.

Boisen et al in a paper entitled "Novel AFM Probes with directly fabricated tips", J. Micromechanical Microeng., 6(1):58, 1996, disclose solid micro-needles and methods of making such. In particular the needles have what is referred to as "rocket tips", and are made by an isotropic-anisotropic-isotropic etch sequence.

U.S. Pat. No. 5,855,801 (Lin et al) discloses a method of fabricating a microstructure. The method includes providing a substrate for forming an interface region and an elongated portion extending away from the interface region. A patterned, non-planar etchable structure is formed on one side of the elongated portion of the substrate. An unetchable membrane layer is deposited atop the etchable structure. At least one etching hole is formed in the membrane layer. The etchable structure is etched by placing an etchant into the etching hole to form a cavity underneath the membrane layer, thereby producing a shaft.

WO 2003/015860 (Stemme et al) discloses a method of making a needle having side openings. It comprises providing a mask on the front side of an etchable wafer such that the vertical projection of said mask at least partially covers the extension of a hole made in the back side. Said mask is isotropically underetched to remove wafer material. An anisotropic etch forms a protruding structure. Optionally a second isotropic etch on said protruding structure exposes the blind hole. Optionally a final anisotropic etch extends the needle without forming side openings. The position and extension of the mask relative the position and dimension of the hole is such that said side openings form during either said anisotropic etc or said second isotropic etch.

U.S. Pat. No. 6,334,856 (Allen et al) discloses a method for making a microneedle. It includes forming a micromold having sidewalls which define the outer surface of the microneedle, electroplating the sidewalls to form the hollow microneedle, and then removing the micromold from the microneedle.

U.S. Pat. No. 6,533,949 (Yeshurun et al) discloses a method for processing a wafer to form a plurality of hollow microneedles projecting from a substrate includes forming, by use of a dry etching process, a number of groups of recessed features, each including at least one slot deployed to form an open shape having an included area and at least one hole located within the included area. The internal surfaces of the holes and the slots are then coated with a protective layer. An anisotropic wet etching process is then performed in such a manner as to remove material from outside the included areas while leaving a projecting feature within each of the included areas. The protective layer is then removed to reveal the microneedles.

A general review on micro needles is found on the internet at the site: http://www.mne.umd.edu/

A problem with prior art devices having micro-needles used in the medical field is to achieve appropriate penetration of the outer skin layer, the stratum corneum. In particular it is important to avoid deep penetration so as to intervene with the nerves.

SUMMARY OF THE INVENTION

Thus, an object of the present invention is to provide new methods for making devices having micro-needles wherein the problems of the prior art devices, such as bad or unsatisfactory penetration of the stratum corneum, are eliminated or reduced.

In a first aspect, the present invention provides an improved method of making micro structures protruding from a surface, such as micro needles, and having an obliquely cut tip, resembling a tip on a cannula.

The method according to the invention in its first aspect is defined in claim 1, and comprises making vertically protruding elements on a substrate, said elements having a tip comprising at least one inclined surface and an elongated body portion extending between said substrate and said tip, the method comprising, an anisotropic, crystal plane dependent etch forming said inclined surface(s), and an anisotropic, non crystal plane dependent etch forming said elongated body portion, combined with suitable patterning processes defining said protruding elements to have a predetermined base geometry.

Preferably the method comprises providing an etchable substrate having a first side and a second side at least one side of which is single crystalline, patterning said substrate on said single crystalline side to form an etching mask so as to expose selected areas thereof, performing an anisotropic etching process through said mask to expose a selected crystal plane of said single crystalline substrate to provide at least one inclined surface, selectively patterning said inclined surface(s) resulting in a pattern defining a base geometry for the protruding element to be made, performing an anisotropic etching procedure to remove material essentially in the vertical direction only so as to leave vertically protruding elements according to said pattern.

Preferably the method further comprises aligning the pattern to selected crystal orientations of said substrate.

The patterning step further comprises using, for the mask, a material that resists the etching that provides the inclined surface.

The mask preferably comprises areas having at least one edge aligned with the crystal orientation of the wafer, i.e. parallel with at least one crystal plane.

Suitably the mask comprises discrete areas of mask material for defining a protruding element having inclined surfaces.

The mask can comprise open areas exposing the wafer for defining depressions having inclined surfaces.

The step of patterning the inclined surface(s) may comprise providing a uniformly thick masking layer by spraying or spinning.

The etching to provide the inclined surface(s) can be performed by using a wet etch, preferably selected from aqueous KOH, NaOH, TMAH, EDP, most preferably the etch is a KOH etch.

Suitably the etching to provide the vertically protruding elements is performed by using a DRIE etch.

Alternatively the substrate is a SOI wafer.

The finished wafer should be at least partially metallized to provide connection between the first and the second side of the wafer.

The needles can be made both as solid and as hollow needles, the latter form being suitable for delivering fluids, e.g. drugs to a patient through the skin. The former, i.e. solid needles can be used for electrical applications, e.g. impedance and resistitvity measurements, measurements of biopotentials (EEG, EKG, EMG etc.). Solid needles can also be used for applications such as emitters.

Solid needles can also be used for pretreatment of the skin instead of using sand paper, which is common today, for removing the outer skin layer so as to enable direct uptake of a drug applied to the skin.

An advantage of the method and the devices obtained therewith according to the first aspect of the present invention over prior art methods is i.a. that an improved penetration of the outer skin layer is achieved. The new method enables manufacturing in high yields.

In a second aspect, the present invention provides an improved method of making micro needles having a polygonal, such as square, rectangular etc., base and a pointed tip, the needles being either solid or hollow.

An advantage of the method and devices obtained therewith according to the second aspect of the present invention over prior art methods is that improved cutting in the tissue is achieved by virtue of the polygonal shape forming edges capable of cutting through tissue, thereby further improving the penetration performance of the needles.

In a third aspect, the present invention provides a method of making a device for electrical measurements, e.g. impedance measurements. The method enables the manufacture isolated groups or arrays of needles integrated on one chip, which provides for well defined distances between needles, and the groups/arrays of needles. On the other hand manufacture of electrodes having single groups or arrays of micro-needles, e.g. for ECG applications, is also enabled with this method.

As defined in claim 13, the method of making devices for electrical measurements, wherein each device comprises a plurality of micro-electrodes in the form of micro-needles protruding vertically from the substrate, comprises the steps of providing a substrate having a first side and a second side; making the micro-electrodes on the substrate; at least partially metallizing the substrate with said micro-electrodes to provide electrical connection between the first and second sides of said substrate.

Finally there is also provided a method of making rotationally symmetric vertically protruding elements on a substrate, the method comprising the following steps of providing an etchable substrate having a first side and a second side at least one side of which is single crystalline, patterning said substrate on said single crystalline side to form an etching mask so as to expose selected areas of the substrate, performing an anisotropic etching process through said mask to expose one or more selected crystal planes of said single crystalline substrate to provide a plurality of inclined surfaces; performing an anisotropic etching procedure to remove material essentially in the vertical direction only so as to leave vertically protruding elements according to said pattern.

The invention in a further aspect provides a method of making devices for electrical measurements, each device comprising a plurality of micro-electrodes in the form of micro-needles protruding vertically from a substrate, the method comprising the steps of: providing a substrate having a first side and a second side; making the micro-electrodes on the substrate; at least partially metallizing the substrate with said micro-electrodes to provide electrical connection between the first and second sides of said substrate, and further comprising electrically insulating groups of micro-electrodes from each other.

Preferably the method comprises making the micro-needles by a process comprising: patterning said substrate, which has a first side which is single crystalline and a second side, on said first single crystalline side to form a mask so as to expose selected areas of the substrate, whereby the mask defines a device, said device comprising at least two groups of micro-electrodes protruding from said substrate; performing an anisotropic etching process through said mask to expose a selected crystal plane of said single crystalline substrate to provide at least one inclined surface; selectively patterning said inclined surface(s) resulting in a pattern defining a base geometry for the protruding micro-electrodes to be made; performing an anisotropic etching procedure to remove material essentially in the vertical direction only so as to leave vertically protruding micro-electrodes according to said pattern.

The step of electrically insulating the micro-electrodes suitably comprises attaching the wafer to an insulating substrate, such as glass, and removing wafer material between said groups at least down to said insulating substrate.

The electrical insulation between groups of micro-electrodes is preferably achieved by using a SOI wafer as the starting substrate and removing material from the device layer of said SOI wafer at least down to the insulating layer thereof.

There are preferably provided three groups of micro-electrodes for each device.

Before the metallization step, part of the insulator layer of the SOI wafer is suitably removed to expose the silicon underneath the insulator layer, and wherein the metallization is limited to cover the exposed silicon, the needles and the area between the micro-electrodes and the silicon so as to create an electrical connection between the micro-electrodes and the silicon.

The insulator is suitably removed by making a recess through the layer and down to the silicon underneath the insulator layer. Removing can be made by any of sawing, laser cutting, drilling, blasting, or alternatively by etching a recess through the layer and down to the silicon underneath the insulator layer.

The metallization can be made through a shadow mask exposing only those areas to be metallised, or by a lift-off process, wherein before metallization, a resist is applied and patterned to expose only those areas where insulation is to be provided between groups of micro-electrodes, then the entire wafer is metallized, and finally the resist is removed whereby the metallization on top of the resist is removed.

The entire wafer can be metallized; an insulator can be deposited only on those areas between micro-electrodes that are to be electrically insulated from each other; and recesses can be made through the metallization down through the SOI insulator layer and down to the silicon beneath, such that groups of micro-electrodes become electrically insulated from each other.

To make a device for impedance measurements the method can comprise making three groups of micro-electrodes, said micro-electrodes can form one single group constituting one single electrode unit.

The metallization can extend over the micro-electrodes and over the vertical edges connecting said first and second sides.

In one embodiment the substrate is a SOI wafer and connection between the first and second side of the substrate is made by providing an opening through the insulator layer of the SOI substrate down to the silicon beneath the insulator, and then providing a metallization over the micro-electrodes and down into the openings.

In a further embodiment, the substrate comprises wafer through connections, and wherein the micro-electrodes are made in groups on said through connections, such that each group is electrically insulated from each other.

Said through connections can be defined by vertical insulating trenches extending through the substrate, or by cylindrical insulating trenches extending through the substrate.

Alternatively, said through connections are defined by two trenches, one from the front side and one from the back side and extending not all the way through but together forming the required insulation.

To obtain individual chips comprising two or more groups of micro-electrodes, electrically insulated from each other the substrate is cut, preferably to obtain individual chips comprising single groups of needles.

In one embodiment the method is used to make micro-needles that are rotationally symmetric vertically protruding elements on said substrate, the method comprising the following further steps: providing an etchable substrate having a first side and a second side at least one side of which is single crystalline; patterning said substrate on said single crystalline side to form an etching mask so as to expose selected areas of the substrate; performing an anisotropic etching process through said mask to expose one or more selected crystal planes of said single crystalline substrate to provide a plurality of inclined surfaces; performing an anisotropic etching procedure to remove material essentially in the vertical direction only so as to leave vertically protruding elements according to said pattern.

The rotationally symmetric micro-needles suitably have a tip comprising at least one inclined surface and an elongated body portion extending between said substrate and said tip, the method further comprising: an anisotropic etch forming said inclined surface(s); and patterning the formed inclined surfaces to define said protruding elements to have a predetermined base geometry; and an anisotropic etch forming said elongated body portion.

The method suitably further comprises the steps of: providing an etchable substrate having a first side and a second side; patterning the substrate on the single crystalline side to form an etching mask so as to expose selected areas of the substrate; applying a DRIE process through said mask; and tuning the etching parameters so as to cause an incremental lateral displacement of subsequent vertical segments generated in each etching increment, such that effectively a sloping surface is generated, the sloping surface being "stepped" in a micro-scale, and does not follow any crystal plane.

The step-wise procedure preferably involves incremental etching steps, alternating with steps of protecting the vertical walls between etching steps to cause the increments to yield a sloping surface of between 60 and 90°, typically 70-80°.

Suitably, the method comprises subsequent smoothening of the generated surface by further oxidation.

The micro-needles in one embodiment are rotationally symmetrical pyramid needles made by KOH etch without corner compensation, further comprising: providing a substrate which is a (100) silicon wafer; positioning a mask positioned on the substrate; rotating the mask 45° with respect to the wafer flat of the substrate; applying a KOH etch to expose further crystal planes, whereby the further crystal planes will be exposed to the same extent as the (100) plane, hence giving rise to an octagonal pyramid, with essentially exactly the same size and shape, i.e. rotationally symmetric.

Preferably, said micro-needles are uniformly high and preferably uniformly pointed needles, regardless of where on the wafer needles are located, or how close the individual masks are laid out on the wafer, and the method further comprises providing on the substrate a pattern that in addition to defining the needles also defines additional sacrificial structures surrounding the needles; a first anisotropic etch, suitably a dry DRIE, applied to said patterned substrate, preferably a pattern defining circular needles; a second isotropic etch, suitably a wet HNA etch, which etches slightly faster at the top of the "pillar" than at the bottom. In particular said additional sacrificial structures are completely removed during the second etch.

Preferably said additional sacrificial structures are thin walls surrounding the needles, or "dummy" needles located outside the area where the actual needles of the device are located.

In one embodiment a stepped-down portion is made on the substrate, the stepped-down portion having a surface located adjacent the group(s) of needles, and at a lower level than the base surface of the needles, so as to form a location for making electrical connections.

In still a further aspect of the invention there is provided a method of making devices for electrical measurements, each device comprising a plurality of micro-electrodes in the form of micro-needles protruding vertically from a substrate, the method comprising the steps of: providing a substrate having a first side and a second side; making the micro-electrodes on the substrate; making a stepped-down portion on the substrate, the stepped-down portion having a surface located adjacent the group(s) of needles, and at a lower level than the base surface of the needles, so as to form a location for making electrical connections; at least partially metallizing the substrate with said micro-electrodes to provide electrical connection between the electrodes and the stepped-down portion on the substrate, and electrically insulating groups of micro-electrodes from each other. Preferably the metallization extends to said stepped-down surface.

The invention will now be described with reference to the appended drawings.

BRIEF DESCRIPTION OF THE DRAWINGS

FIG. 8b is a side view of a pyramid after etching where the mask is still present on the top of the pyramid;

FIG. 8c is a top view of a pyramid;

FIG. 8d shows a pyramid having "rounded off" corners due to misalignment of mask pattern to the crystal planes of the wafer;

FIG. 8e shows an embodiment using DRIE to obtain a pyramid with sloping surfaces, not corresponding to a crystal plane;

FIG. 8f is a magnified cross-sectional view of the tip area indicated in FIG. 8e showing mask 80, oxide 82 and intersection 84 between oxide layers.

FIG. 8g shows the result after vertical etching;

FIG. 9a-d shows a scheme for corner compensation;

FIG. 9a shows a mask configuration in a top view;

FIG. 9b shows a pyramid resulting from the use of the mask in FIG. 9a;

FIG. 9c1 illustrates masking a square based pyramid;

FIG. 9d1 shows the result of DRIE etching the masked pyramid;

FIG. 9c2 illustrates masking a pyramid with a circular base;

FIG. 9d2 shows the result of DRIE using the mask in FIG. 9c2;

FIG. 18 illustrates using an SOI wafer for making a device for electrical impedance measurements;

FIG. 25 shows a top view of one embodiment an impedance measuring device according to the invention with circular insulation enclosures;

FIG. 26 shows a top view of one embodiment an impedance measuring device according to the invention with insulation enclosures extending across the chip;

FIG. 31 illustrates the provision of electrical connection between needles and the via by metallization;

FIG. 32 illustrates an alternative to the sawing shown in FIG. 29;

DETAILED DESCRIPTION OF THE INVENTION

The expression "single crystalline" is taken to mean an object comprising at least some macroscopic portion thereof that is single crystalline. Standard wafers for semi-conductor manufacturing (including SOI wafers), and rated to be nominally "single crystalline" are regarded as single crystalline for the purposes of this application. An SOI wafer is taken to be "single crystalline" as long as at least one of its layers is essentially single crystalline.

All embodiments shown are repeating units over an entire wafer.

The main concept forming the basis for the present invention in its first aspect is to provide inclined surfaces on a substrate by etching, and to use substrates having inclined surfaces as the starting substrates for the further processing to achieve the desired structures.

On the inclined surfaces there is provided a mask by appropriate patterning techniques (such as lithography using photo resists), whereby suitable etching through the mask will provide the desired structures in question, such as needles or other structures, protruding out from a base in a desired configuration. In particular the use of such inclined surfaces will enable the manufacture of a cannula type of tip on a hollow needle, i.e. the needle is obliqely "cut" at the tip. For solid needles it is possible to provide an oblique end surface at the tip of the solid needle, a feature that is suitable for electrical applications. If the needle base is made square or at least having edges, rather than a circular base, the needle will have better cutting performance, which is important in medical applications.

The main working substrate for producing the desired micro structures is normally (single) crystalline silicon in the form of wafers. These wafers can have surfaces exhibiting different crystal orientations such as <100>, <110>, <111>, off-cut etc.

However, any other crystalline material that can be subjected to the same or similar processing techniques are equally well suited, the specific choice being dependent on the end use or final application of the structure being manufactured. Thus, materials such as $SiO_2$ (quartz), diamond and/or SiC (for emission needles or for needles subjct to high abrasion), GaAs, and the like can be used for specific applications.

In particular it is very useful to employ so called SOI wafers (Silcon On Insulator) as a starting substrate, since SOI wafers will provide well defined etch stop layers. Such stop layers are practical for the purpose of defining dimensions (i.e. heights, widths, depths of recesses etc.) of the structures being made, and for eliminating certain unwanted side effects of etching.

Figure 1A:
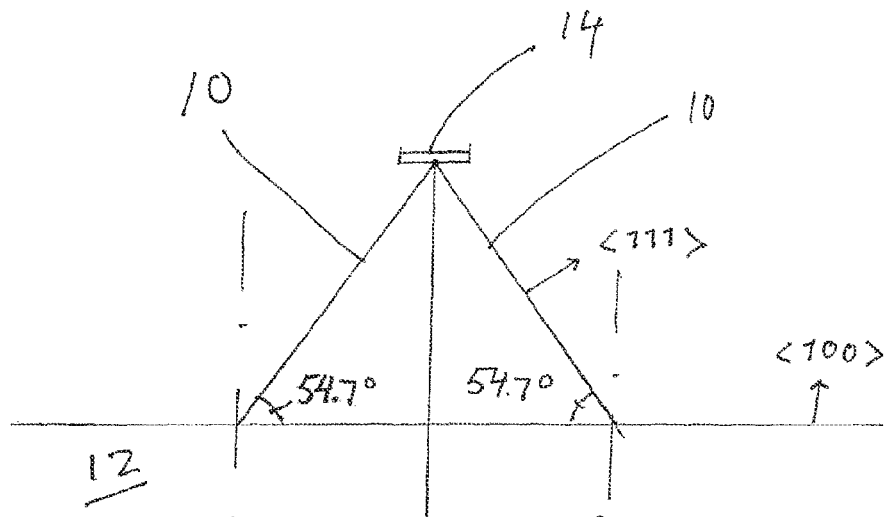
FIG. 1a is an end view of a pyramid/ridge after etching to expose the <111> crystal planes.
Figure 1B:
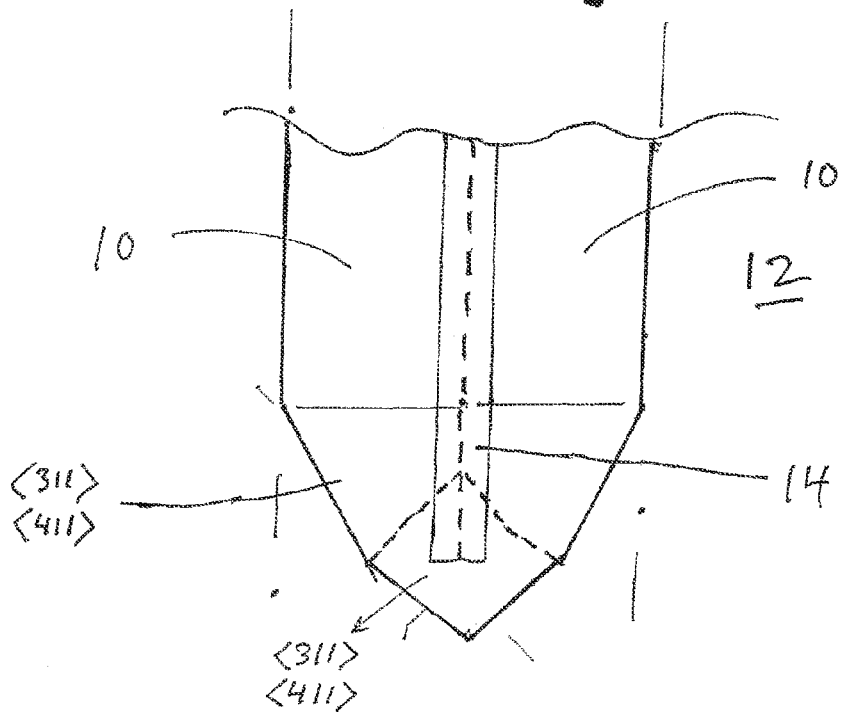
FIG. 1b is a top view of a structure of FIG. 1.

Reference is now made to FIGS. 1a and 1b, FIG. 1a showing a side view of (a part of) an etched wafer (actually showing a ridge, made by etching, from one end), and FIG. 1b a top view of the same wafer. In order to achieve the inclined surfaces 10 an anisotropic etching process, normally using aqueous KOH, is performed. However, other kinds of etching systems can be used, exemplified by KOH, NaOH, TMAH, EDP, and others; KOH being the preferred choice). This etching process will act on a silicon wafer 12 in which the <100> plane is horizontal. A mask 14 (e.g. $SiO_2$ or $Si_xN_y$), that resists the etching medium, in the form of an elongated strip is provided on the <100> surface. Applying the etch will then provide a "ridge" like structure having sloping/inclining sides surface starting from under the mask and following the <111> plane at an angle of 54.7° down to the horizontal <100> plane. This is schematically illustrated in FIGS. 1a and 1b. The height of the pyramidal structure will of course depend on the etching parameters, such as time, concentration, temperature. If an SOI wafer with a well defined Si (device layer) thickness is used the height could be controlled very accurately, since the oxide layer will act as an etch stop. Height control is a major problem with prior art methods relying on dry DRIE under-etch, since the height will vary in dependence of location on the surface and how closely spaced the needles are.

However, it is possible to make needles having inclined tip portions, similar to the embodiment shown in FIG. 1, but instead of using a wet KOH etch a DRIE etch can be used. This might be thought of as surprising since the DRIE is allegedly used as an anisotropic etch in this application for the purpose of the invention. However, as the skilled man will appreciate, the DRIE is a step-wise procedure involving incremental etching steps, alternating with steps of protecting the vertical walls between etching steps. This is normally referred to as the "Bosch process", and is subject of patent protection, DE-424 10 45. It is to be understood that the individual incremental etching steps remove very little material in each step.

Thus, for the purpose of making an "anisotropic" etch, the process parameters are tuned such that the result will be an etching groove having essentially vertical side walls.

On the other hand if parameters are slightly adjusted it will become possible to cause the increments to yield a sloping surface of between 60 and 90°, typically 70-80°, which can then be used together with suitable mask works to create a needle resembling the one of FIG. 1.

Thus, a method for making rotationally symmetric vertically protruding elements on a substrate in the aspect discussed above, comprises providing an etchable substrate having a first side and a second side at least one side of which is single crystalline. The substrate is patterned on the single crystalline side to form an etching mask so as to expose selected areas of the substrate. A DRIE process is applied through said mask. The etching parameters are tuned so as to cause an incremental lateral displacement of subsequent vertical segments generated in each etching increment, such that effectively a sloping surface is generated, the sloping surface being "stepped" in a micro-scale, and does not follow any crystal plane. These microsteps are often referred to as "scallops", and can be smoothened out by further oxidation.

Figure 2A:
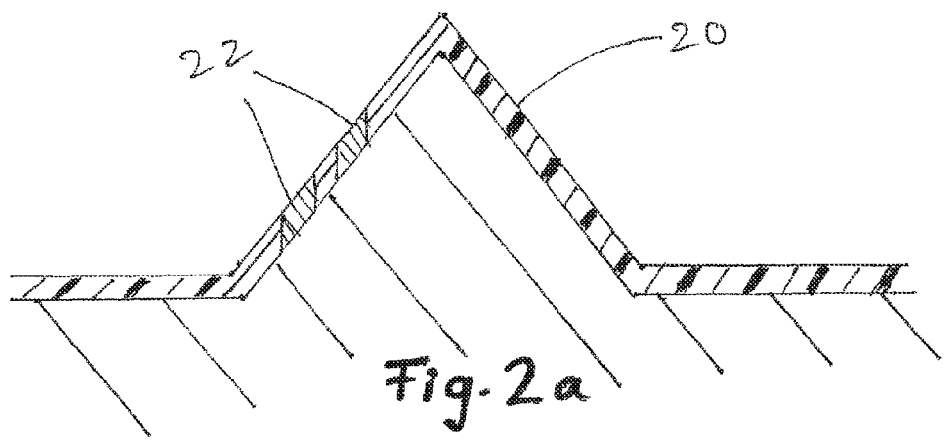
FIG. 2a is a cross section through a pyramid with patterns provided for definition of needle geometry.
Figure 2B:
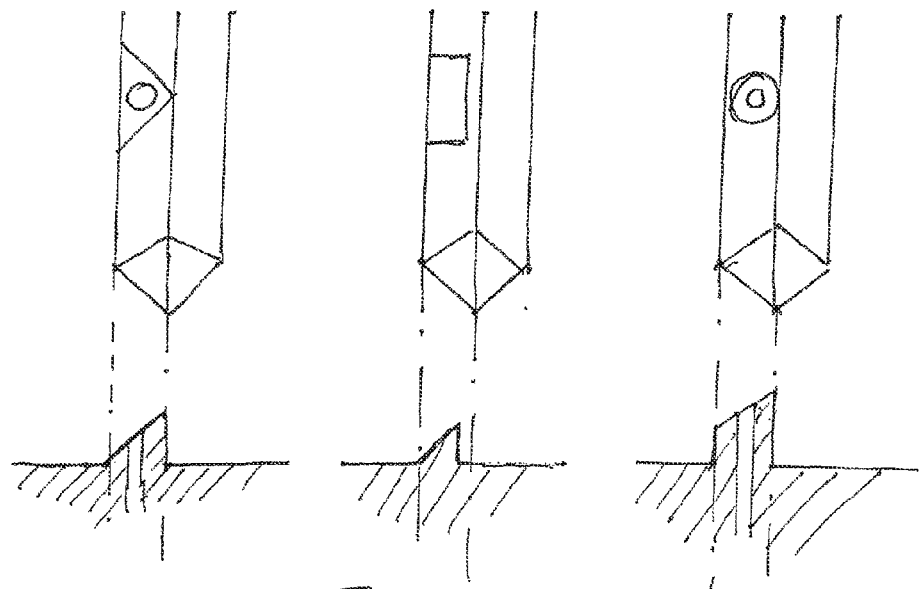
FIG. 2b is shows top views of differently patterned structures.

Reference is now made to FIGS. 2a and 2b.

When the desired starting structure, i.e. comprising protruding members having inclined side surfaces, has been successfully made, the inclined surfaces must be appropriately patterned in order to define the final structures, e.g. needles having a "cannula" type of tip, or simply solid needles having a oblique tip surface.

This requires a lithographic procedure capable of providing a uniformly thick masking layer 20 on a sloping surface. Particulars of such a procedure is not part of the present invention per se. Normally the entire surface is covered with a photo sensitive resist 20, suitably by a spraying technique (known per se), or by spinning deposition, which is then exposed to light such that only the desired mask portions defining the structures will be developed 22. The portions of resist that does not define the desired pattern will be removed by dissolving/washing. The resist is shown schematically in FIG. 2a before removing the non-pattern portions. FIG. 2b shows various possible geometries.

A particular problem that may have to be addressed in this connection is the generation of "ghost" patterns. These may arise due to reflections from the inclined surfaces on which the mask patterns are to be made during light exposure. Namely, if adjacent pyramidal ridges are located close enough to each other, light impinging on a sloping pyramid surface may be reflected further and create an image on an the adjacent pyramid. To avoid this effect it may be necessary to provide anti-reflective coatings on or underneath the resist layer.

Another method could be to arrange the ridges or pyramids from which the needles are made in a staggered configuration, such that reflections from one pyramid will pass between adjacent pyramids. Alternatively, one could ascertain that the pitch between pyramids is sufficiently large that reflections will pass over adjacent pyramids.

Figure 3A:
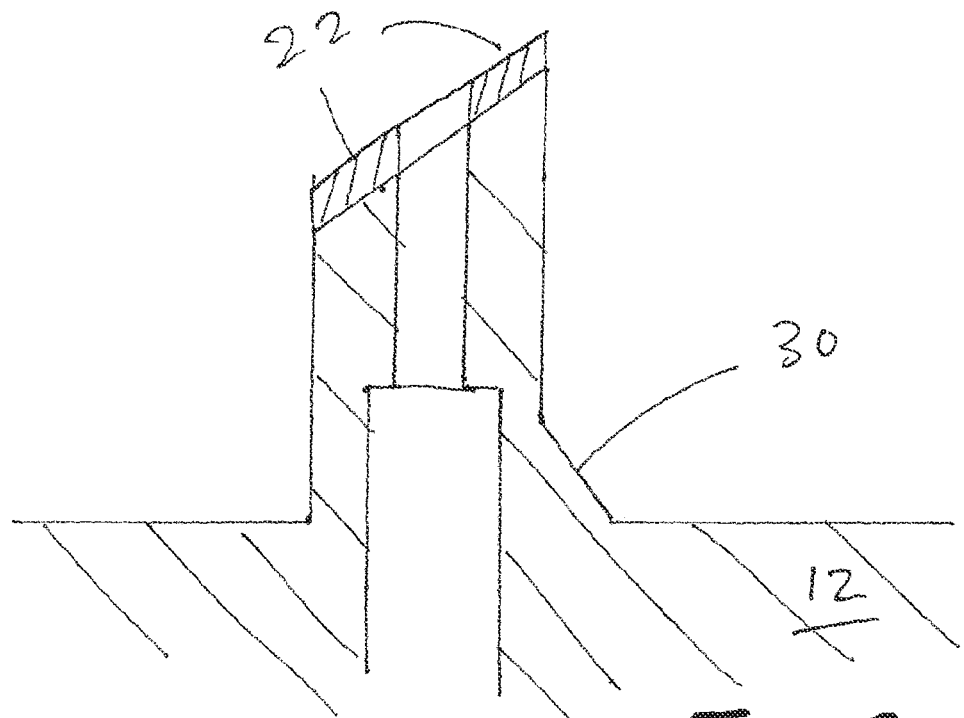
FIG. 3a is a cross section through a needle after vertical etch.

A DRIE (Deep Reactive Ion Etching) etch is then performed. DRIE as it is performed for this purpose is effectively anisotropic (it entails alternating etching and passivation steps; small increments of isotropic etching followed by a passivation by a polymer), i.e. the result will not depend on crystal plane orientation, and therefore the mask that has been provided on the wafer surface will define vertical walls of the protruding structure. However, the opposite sloping surface, i.e. the surface that is not masked to yield a protruding structure, will remain as a sloping surface at the base of the structure, by virtue of the DRIE being anisotropic, i.e. it will remove material at the same rate in the horizontal direction. Thus, portions of the wafer material located at a higher level than other portions, will maintain the relative levels when the DRIE etch is finished, as can be seen in FIG. 3 at 30. Also, in FIG. 3 the mask 22 has not been removed yet.

Figure 3B:
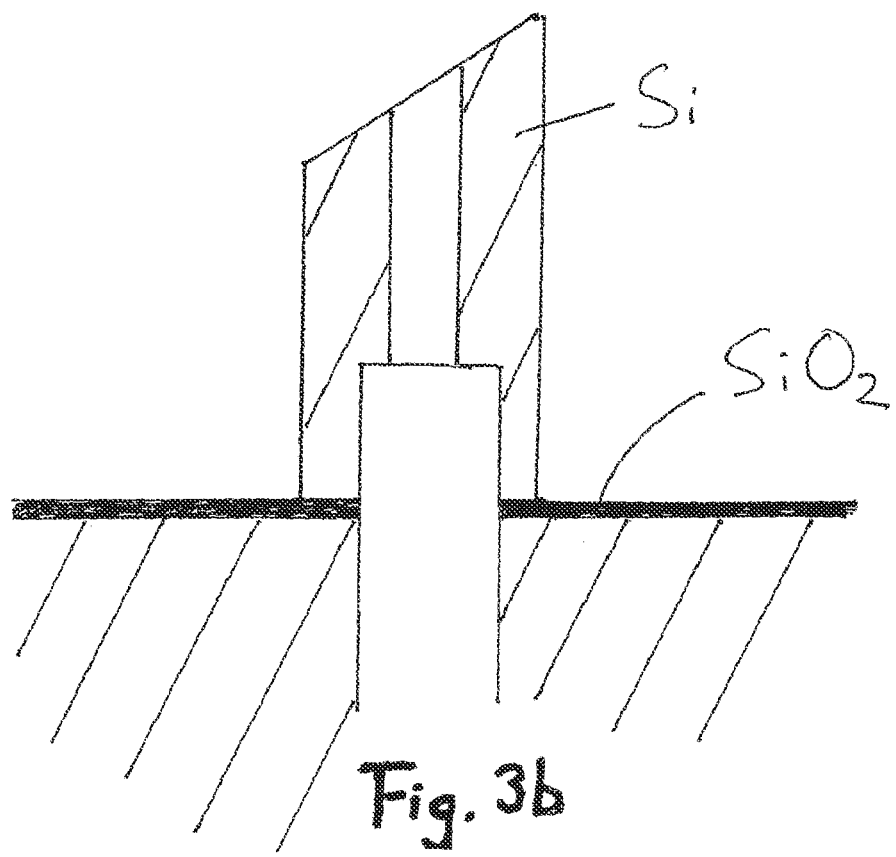
FIG. 3b illustrates the benefit of using an SOI wafer.

For better control of needle height, an SOI wafer can be used, see FIG. 3*b*. The $SiO_2$ layer beneath the "device layer" will act as an etch stop, such that the height will be basically equal to the thickness of the device layer. Using an SOI wafer will also make possible the elimination of the residual sloping surface 30.

A particular problem can arise if extremely small (in the order of <1 µm in diameter) particles of residual resist from the mask remains on the surfaces. These particles will result in structures referred to as "grass" 32, see FIG. 3*c*, i.e extremely thin straws of silicon extending vertically from the wafer after the DRIE etch. If an SOI wafer is used it is very easy to remove such residual "grass" from the wafer.

A feature of the above described method is that the structure, e.g. needle, can be given virtually any shape, such as round, elliptic, square, triangular, rectangular, polygonal etc., see FIG. 2*b*. If the mask defining the shape is rectangular or square, the end result will be a structure much resembling a knife-edge, and if the mask is round (the actual shape on the sloping surface would have to be elliptic of course), the end result will be a needle.

If the mask defining the outer boundaries of the structure comprises an opening, the DRIE will remove material through said opening and will form a vertical channel in the structure.

Of course also the shape of the channel, i.e. its cross-section geometry can be varied at will, such as to render it circular, elliptic, square or rectangular, or polygonal by shaping the opening in the mask appropriately.

The depth of the central channel through the structure will preferably be equal to the height of the structure, if the channel is made at the same time as the needle itself, which would be the normal way of doing it. The diameter of the central hole will then be of importance. A too narrow channel would restrict the rate of removal of material during the etch, and thus the etching rate might be slower than outside the needle, which of course would render the hole having a depth differing from the depth to which the surrounding etch reaches. It might be possible to perform the DRIE in two separate steps, one for the definition of the needle exterior shape, and, after appropriate masking, performing a second DRIE to make the channel, which could then be made to extend all the way through the wafer or substrate. However, this latter approach would be more time consuming, and would require alignment of patterns between steps, and most likely would not be an economically viable method, other than for very specific purposes.

Instead a channel extending all the way through the wafer is achieved by making a second hole from the back side, e.g. using DRIE. One advantage the present method is that it allows misalignment to some degree, and thus no accurate marking for the purpose of performing alignment is required.

A further advantage is that the hole from the backside can be made with a larger diameter, which means that the etching is faster (>2 times as fast), meaning higher through-put and thereby a cheaper process.

Figure 4:
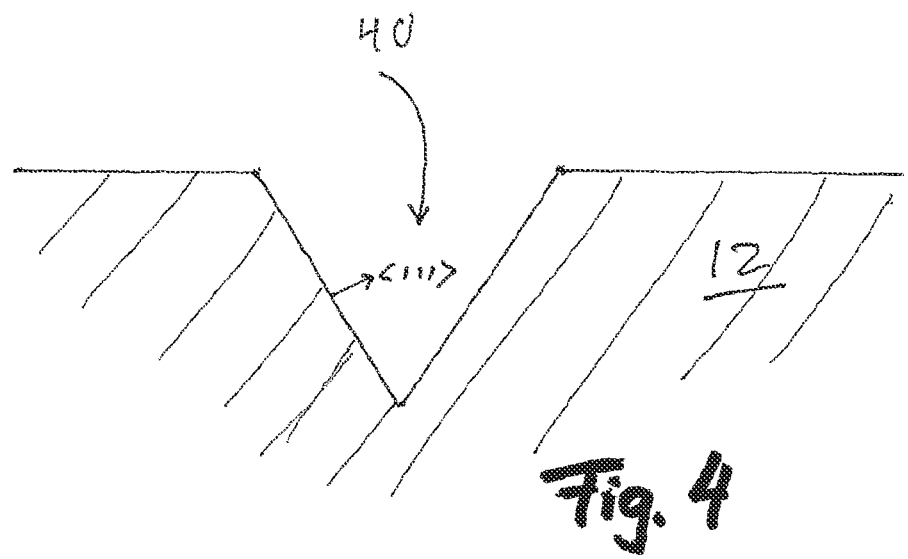
FIG. 4 illustrates a further embodiment of the method wherein recesses are used instead of ridges/pyramids as starting substrate.

In an alternative embodiment of the above described method, the starting substrate for making protruding structures with obliquely cut tips comprises V-shaped recesses 40 or grooves in the wafer 12 instead of the protruding "ridges" discussed above, see FIG. 4.

Figure 5:
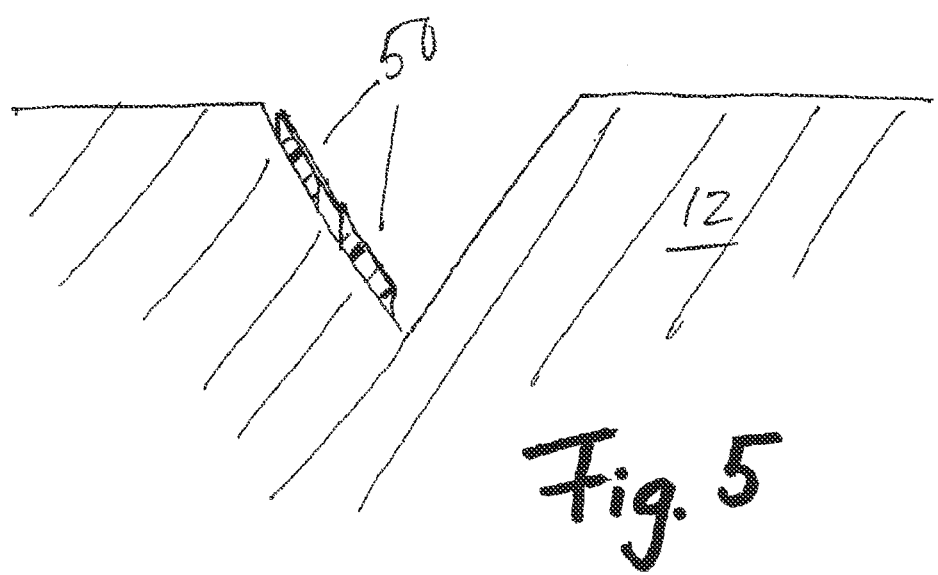
FIG. 5 shows a recess of FIG. 4 provided with a mask for needle definition.

Such recesses are made by masking a starting wafer so as to leave elongated slits mask material, i.e. a "negative" of the mask from the first embodiment. Subsequently this masked wafer is subjected to an anisotropic KOH-etch, which will act selectively on the exposed wafer material through said slit, thereby yielding a V-groove 40 wherein the sloping surfaces correspond to the <111> planes of the crystalline wafer. Similarly to the previous embodiment, the wafer, now comprising a plurality of V-grooves, is appropriately masked, suitably using a resist that is sprayed on or spin deposited for achieving a uniform layer of resist, to define the geometry of the desired structure, analogously to the first embodiment. In FIG. 5 the cured mask portions 50 defining the desired needle are shown. A DRIE etch follows whereby wafer material are etched away to form vertically protruding structures, e.g. needles 60.

Figure 6A:
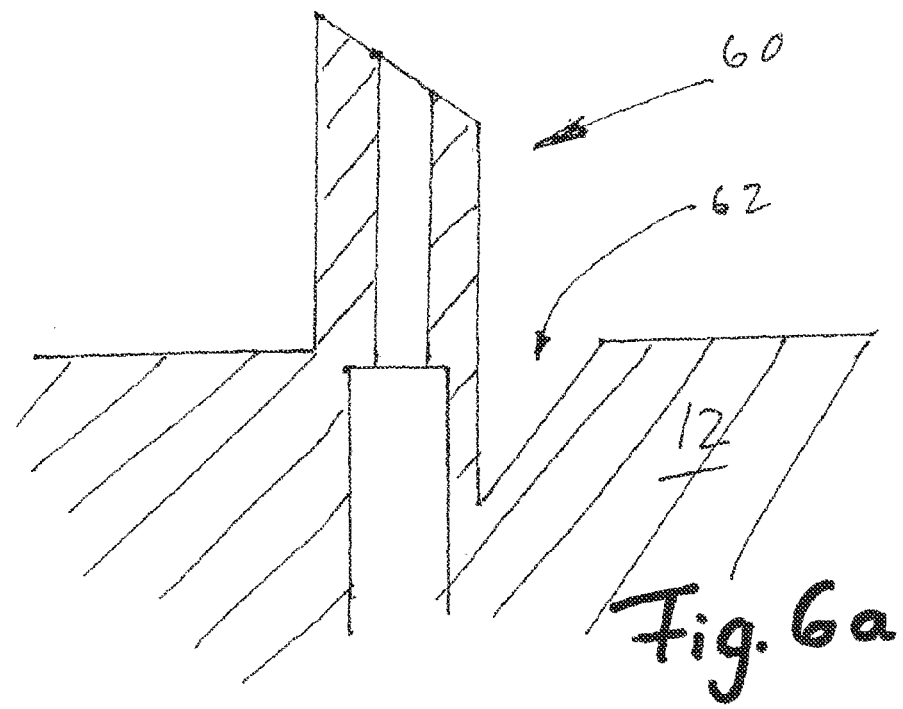
FIG. 6a shows a hollow needle made according to the embodiment of FIGS. 4-5 in cross section.

It should be noted, however, that in this embodiment, for the same reason as in the above described embodiment, i.e. the isotropic nature of the DRIE method, there will always remain a V-groove 62 adjacent the protruding structure, as can be seen in FIG. 6.

Figure 6B:
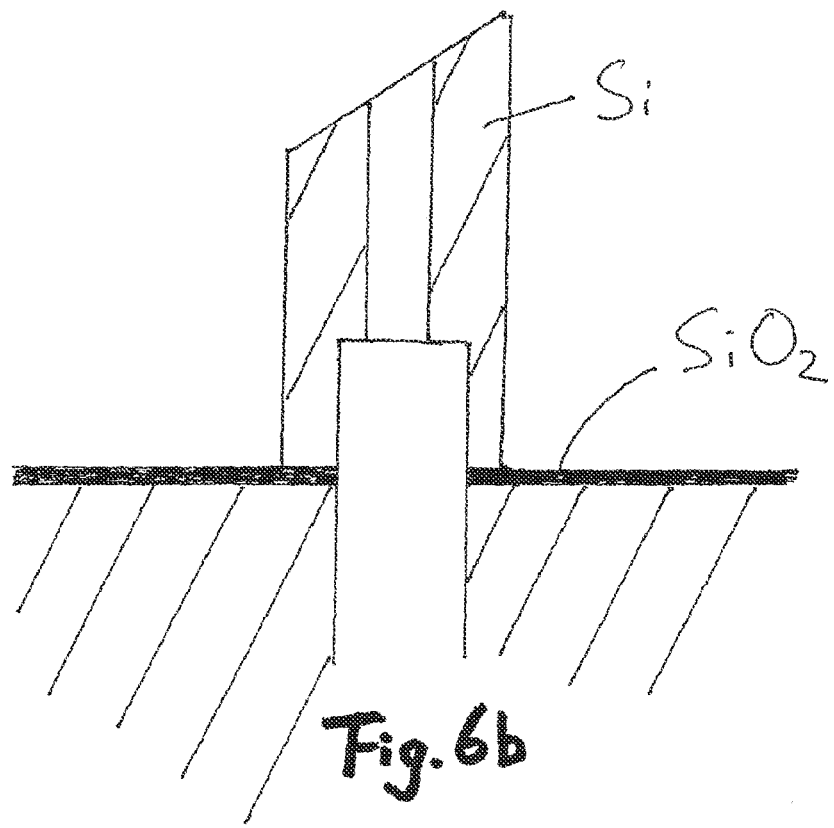
FIG. 6b shows a variant of the embodiment of FIG. 6a using a SOI wafer.

In a similar manner as in the method described in connection with FIG. 3, also in this case the residual V-groove can be eliminated if a SOI wafer is used as starting wafer, see FIG. 6*b*. Thereby the $SiO_2$ layer will prevent the etch from excavating more material. When the hole is made from the backside, of course a separate step for penetrating the oxide layer may be necessary.

Figure 7:
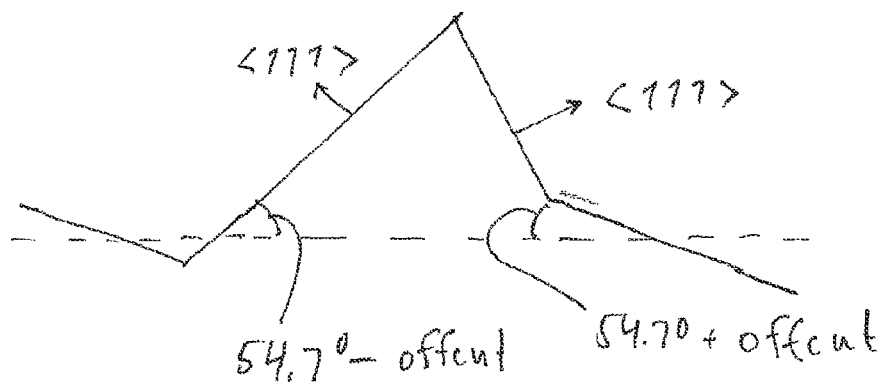
FIG. 7 illustrates using "off-cut" wafers for making tips having variably inclined tip surfaces.

In a further embodiment of the method according to the invention, the starting substrate has a crystal orientation different from standard. Normally the wafer surface would correspond to the <100 plane. However, if the wafer is cut from the single crystal "ingot" at an angle deviating from the <100> surface, which is referred to as an "off-cut" angle, the crystal planes determining the inclined surfaces during the isotropic etch, will be exposed at an angle the will differ from the 54.7° (<111> plane) by said "off-cut"-value. This is illustrated in FIG. 7*a*. The "off-cut" angle is normally 5-15°. Note however that it will still be the <111> plane that forms the inclined surface.

Thus, if such an off-cut wafer is used as a starting substrate, the methods according to the above described embodiments will generate needles the inclined tip surfaces of which will have an angle differing from the <111> angle (i.e. 54.7°) by the "off-cut" value, as shown in FIG. 7*b*.

In a further aspect of the invention needles can be made from substrates having no inclined starting surfaces, i.e. a conventional flat wafer is used as starting substrate.

Figure 8A:
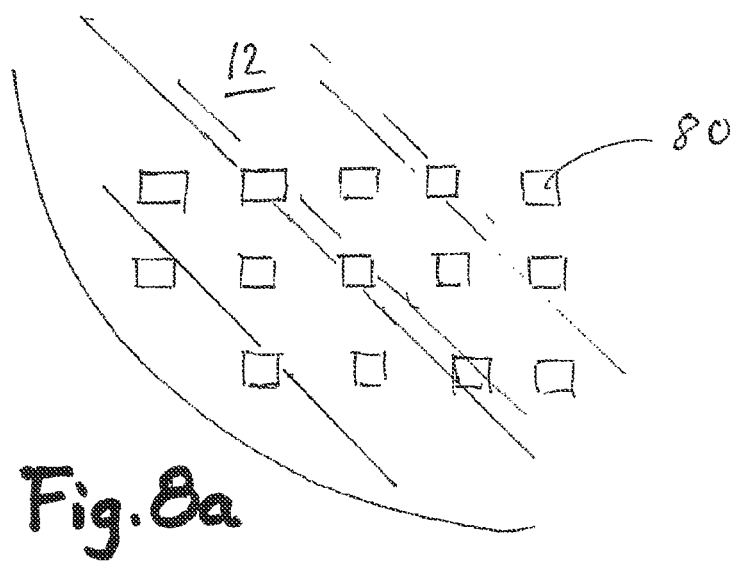
FIG. 8a shows a wafer in a op view with a mask pattern for making pyramids.

Thereby the mask pattern can consist of square patches of e.g. $SiO_2 Si_xN_y$, 80, as schematically shown in FIG. 8*a*. Applying a wet anisotropic etch (e.g. KOH) will give rise to an under-etch of the mask to provide a pyramidal structure (see FIG. 8*b*) wherein the sloping walls correspond to e.g. <111> planes of the wafer crystal.

However, in order to achieve a perfect pyramid, as illustrated in a top view in FIG. 8*c*, the mask will have to be very accurately orientated with respect to the orientation of crystal planes in the wafer. If the orientation is incorrect, the KOH etch will expose other crystal planes than the <111> planes, namely planes like <411> and <311>. In such a case, the intersections between <111> planes will be "rounded off" and the end result will resemble the shape shown in FIG. 8d, i.e. a polygonal pyramid. In particular this latter case will give rise to round tips, as opposed to the square tips resulting in FIG. 8c.

The degree of "rounding off" strongly depends on the etch that is used. For KOH there is a large degree of freedom on rounding due to the etching speed ratio <411>/<100>. The speed strongly depends on concentration of the etching media.

Provided that the orientation of the mask relative to the crystal planes is successfully made, and the structure disclosed in FIG. 8c is achieved, a dry anisotropic etch (i.e. independent of crystal plane) is performed to etch the base, i.e. the vertical pillars are made, and the result will be the structure shown in FIG. 8g.

When the mask 80, i.e. the pattern defining the needles, has been removed etching, the tip of the needle will not be pointed, but instead it will exhibit a top surface which is square, see FIG. 8c. In order to sharpen the tip, an oxidation can be performed before removing the mask, by heating in an oxygen atmosphere, thereby oxide 82 will grow inwards under the mask 80, and when the oxide from different directions meet under the mask the intersection 84 between the oxide layers will cause the tip to become pointed.

This method enables the manufacture of solid needles having a square base using a single mask.

A rotationally symmetrical pyramid needle can be obtained by KOH etch without corner compensation. An example is shown in FIG. 8e. To obtain this structure, a mask is positioned on a wafer, the mask being similar to that used for making the needles of FIGS. 8c-d. However, in this case the mask is rotated 45° towards the wafer flat (i.e. the alignment feature provided on the wafer showing crystal orientation) on a (100) silicon wafer. Applying a KOH etch will expose further crystal planes, but due to the exact rotation of the mask (through an angle of 45°) the further crystal planes will be exposed to the same extent as the (100) plane, hence giving rise to an octagonal pyramid, with essentially exactly the same size and shape, i.e. rotationally symmetric.

An alternative embodiment of the above described method employs two masks as can be seen in FIG. 9a-c.

Thereby, a first mask 90 having a shape generally resembling an "X" is provided on a planar wafer, FIG. 9a, and a KOH etch is applied. The legs 92 of the "X" form corner compensation structures, and will have the effect of protecting the wafer material during the etch such that the unwanted crystal planes (e.g. <311> and <411> etc.) will not be exposed, thereby avoiding the problem of "rounded off" corners. This will result in a near perfect pyramid shown in FIG. 9b.

In order to ascertain a near perfect pyramid without rounded corners, the width (w) of the legs (corner compensation structures) should be twice the height (h) of the pyramid itself, i.e. w=2 h.

In order to make the base, i.e. the cross-sectional shape of the needle, lithography (e.g. photoresist) is employed to define the geometry of the base, which can be given any geometry. Thus, resist 94 is applied to the wafer comprising protruding pyramids, the desired geometry is exposed onto the resist and developed. FIGS. $9c_1$ and $9d_1$ show an example wherein the entire pyramid is covered with a "square shaped" resist layer, and FIGS. $9c_2$ and $9d_2$ show the case where the resist is given a circular shape.

Finally a DRIE etch is applied to make the vertical base which will result in needles having a square base (FIG. $9d_1$) or a circular base (FIG. $9d_2$), respectively.

In a further embodiment, which is a variation of the above described embodiment, two masks are provided on a flat substrate.

Figure 10A:
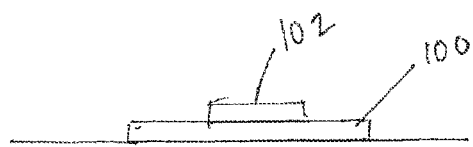
FIG. 10a-f illustrates an alternative approach to that of FIGS. 9a-d.
Figure 10B:
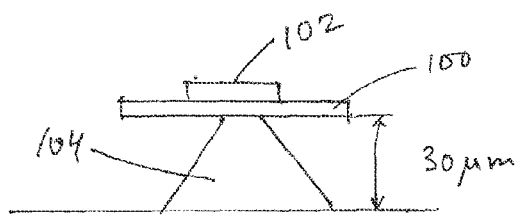

A first "X"-shaped mask 100 (like the mask 90 in FIG. 9a) is applied (see FIG. 10a), suitably by the deposition of SiN, or by providing a thin $SiO_2$ layer. A second mask 102 defining the base geometry (square or circular etc.) is applied, suitably an oxide is used (e.g $SiO_2$ that is thermally oxidized), but SiN can also be used. A KOH etch is applied to make a pyramid structure 104, suitably the pyramid will be approx. 30 μm high, as shown in FIG. 10b. When the structure according to FIG. 10b is achieved the wafer is subjected to a "blank etch" which removes the first mask (SiN) but leaves the second mask very nearly unaffected. The result is the structure shown in FIG. 10c.

However, if the corner compensation structures (i.e. the "legs" of the "X" shaped structure) are left and thus not removed, a DRIE etch would result in "wings" extending out from the central body portion of the needle, a feature which could be beneficial for enhancing penetration performance.

Figure 10C:
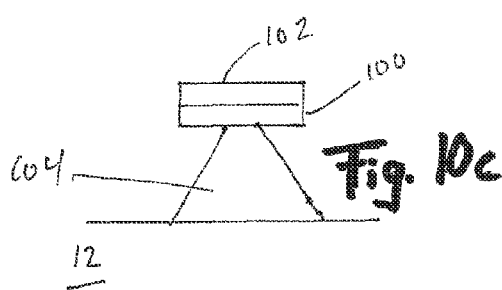
Figure 10D:
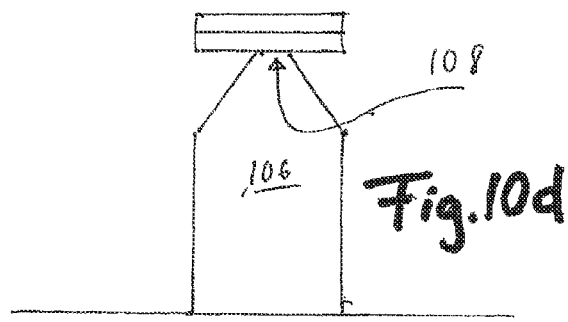

In the same manner as in the previous described embodiments a DRIE etch is performed on the structure obtained and shown in FIG. 10c, which will remove material in the vertical direction independent on crystal plane orientation, as shown in FIG. 10d. This will result in a vertically protruding needle 106 having a base geometry corresponding to the second mask shape.

Figure 10E:
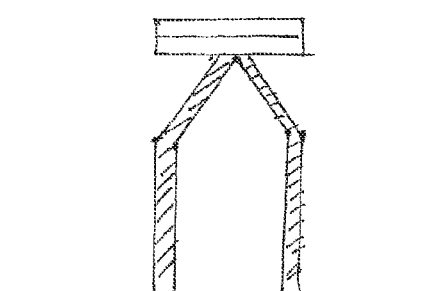
Figure 10F:
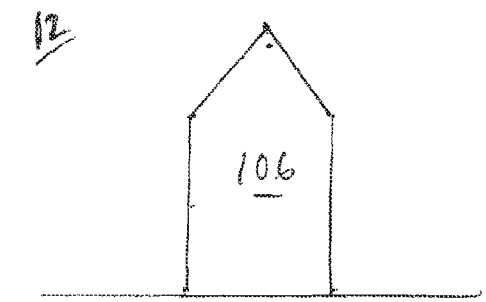

Like in the previously described embodiments the tip at this stage in the process is covered by a mask 100, 102 which will cause the tip to have a flat top surface 108, i.e. it is not as sharp as desired. In order to sharpen the tip a local thermal oxidation is performed, see FIGS. 8e-f and FIG. 10e, and finally the oxide is stripped off, to leave a pointed needle 106, FIG. 10f. A "blank etch" of the oxide removes all oxide present on the wafer.

Figure 11A:
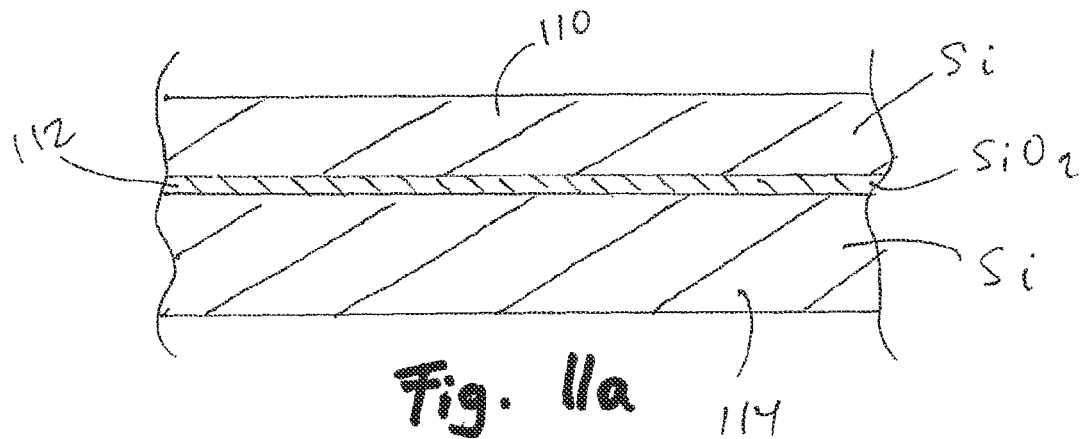
FIG. 11a-c illustrates using an SOI wafer.

For all above described methods and embodiments thereof it is possible to use SOI (Silicon On Insulator) wafers, see FIG. 11a, as a starting substrate. If SOI wafers are used it will become possible to obtain some additional beneficial features. First to be mentioned is that if the device layer 110 of the SOI wafer is used to make the needles, the height can be controlled to a very high degree of accuracy, in particular the needles can be made to have a very uniform height, since the thickness of the device layer which extends down to the insulator 112 ($SiO_2$) is known to high accuracy. The insulator layer of the SOI wafer will function as an etch stop layer. The bottom layer is referred to as a handle layer 114.

Figure 3C:
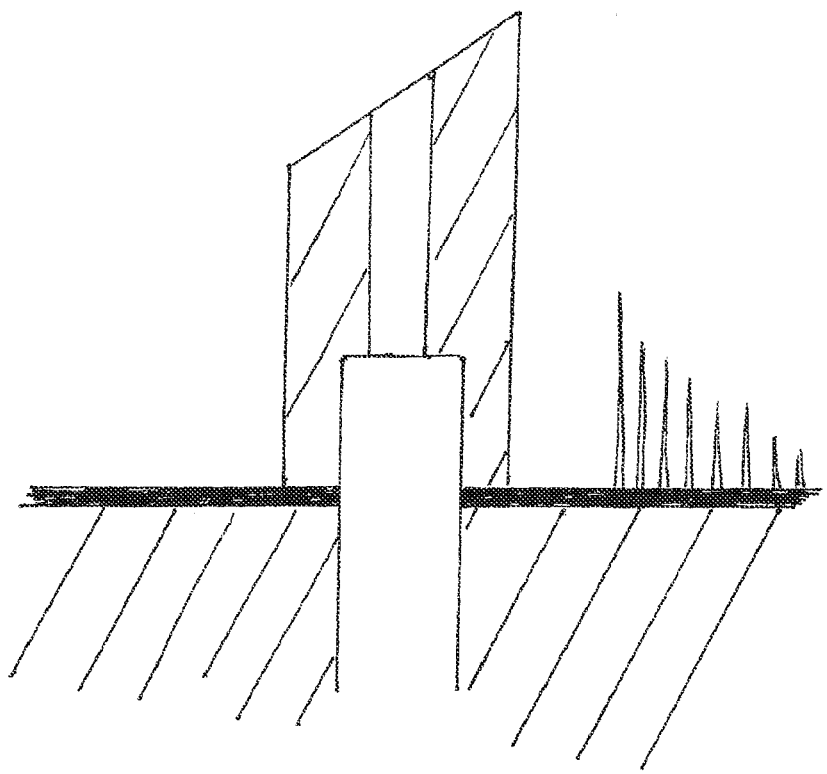
FIG. 3c shows the undesired "grass" formation.

The buried oxide layer in the SOI wafer allows "over-etch" using DRIE for e.g. removing "grass" (see discussion in connection with FIG. 3c).

When the method(s) described above using inclined surfaces for making needles with obliquely cut tips are applied on SOI wafers, it will be possible to make needles of different heights, which are isolated from each other.

Figure 11B:
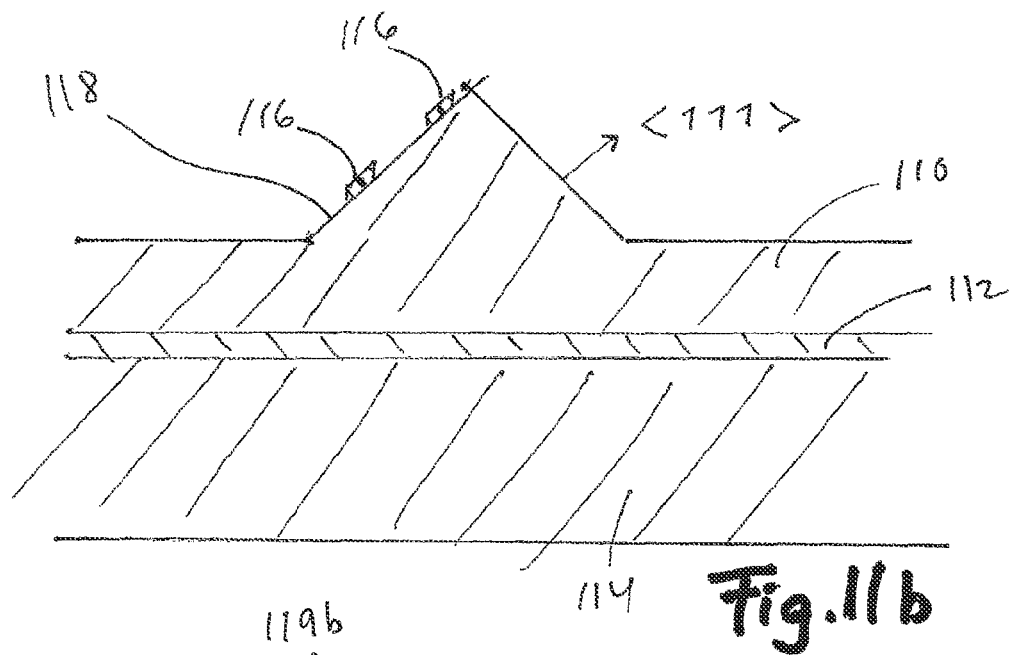
Figure 11C:
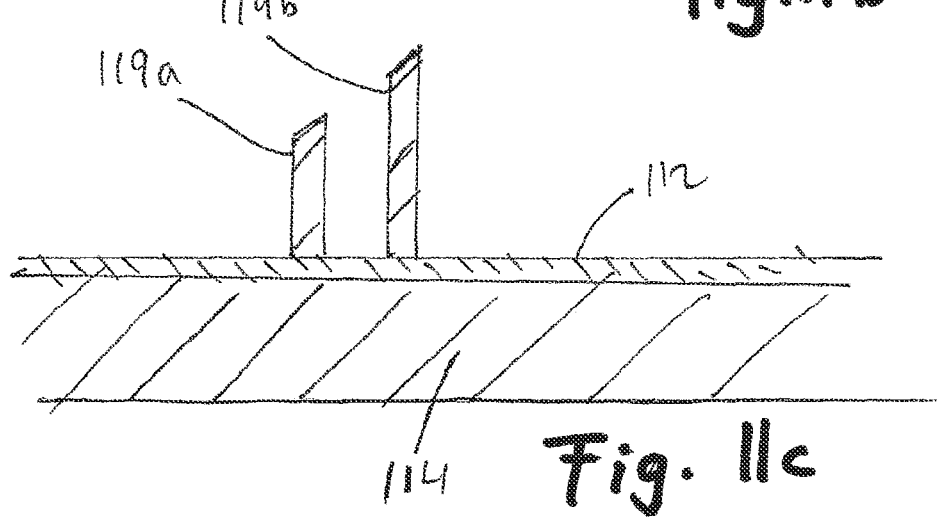

This is illustrated in FIG. 11b-c, wherein an SOI wafer, after having been processed (patterning and isotropic KOH etch) to exhibit ridges wherein e.g. <111> planes are exposed, is patterned with masks 116 at different levels on at least one of the inclined surfaces 118 (FIG. 11b). Applying a DRIE etch will remove material in the vertical direction down to the etch stop (insulator) layer, to result in two needles 119a, 119b of different height, and both having obliquely cut tips, FIG. 11c.

The structure/configuration according to FIG. 11c can be used for the penetration of the skin, whereby the longer needle can be used to stimulate nerves, whereas the shorter needle will not reach down to the nerves and can be used for other purposes.

Furthermore, of course both needles of FIG. 11c could be made to be hollow, by employing any of the methods previously described herein, in which case e.g. the longer needle could be used for the purpose of analyzing blood or glucose in blood vessels, at the same time the shorter needle could be used for injecting e.g. insulin or other medicaments in the skin.

A particular application of the use of the methods according to the present invention, specifically employing the SOI wafer approach as discussed above, is to make electrically isolated groups of needle arrays. Such groups of arrays are suitable for e.g. making impedance measurement chips. This application is the subject matter of a copending Swedish patent application No. 0502761-0 (also published as WO 2007/068433) entitled, "Needle arrays for impedance measurements," which was filed on the same day as the priority application to the present application, in the name of SciBase AB.

Figure 12A:
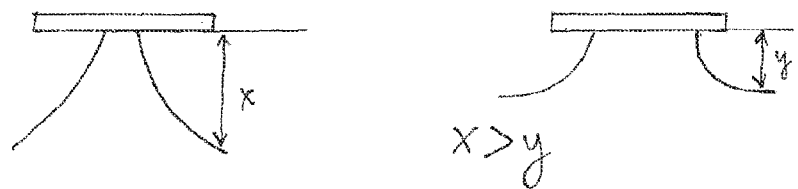
FIGS. 12a-b illustrates different etching rates at different locations.

A problem that exists in prior art methods employing DRIE machines is that an etch sequence of isotropic-anisotropic-isotropic etch (see Boisen et al and Stemme et al, supra) is difficult to control from a process point of view. Namely, the first isotropic etch will vary across the wafer, i.e. different results will be obtained at the edges and at the centre, respectively. Near the edges of the wafer the etch rate in the vertical direction will be higher than at the centre, see FIG. 12a. The result will be longer and more pointed needles (left) at the edges.

The first isotropic etch will also vary in dependence of how the pattern is designed or configured. Namely, masks defining e.g. individual needles that are closely spaced will have a higher etch rate in the vertical direction than in a case with masks that are not so closely spaced, see FIG. 12b. The result is that "dense" patterns will yield higher needles than less "dense".

This adverse "location effect" of the DRIE etch results in needles that have different heights, and also that the needles will become pointed to different degrees, depending on where on the wafer they are located, and how close to each other they are located. This is of course not acceptable from a quality point of view, where uniform needles are essential for the end product or end application. This is an important issue in large volume production.

Figure 12B:
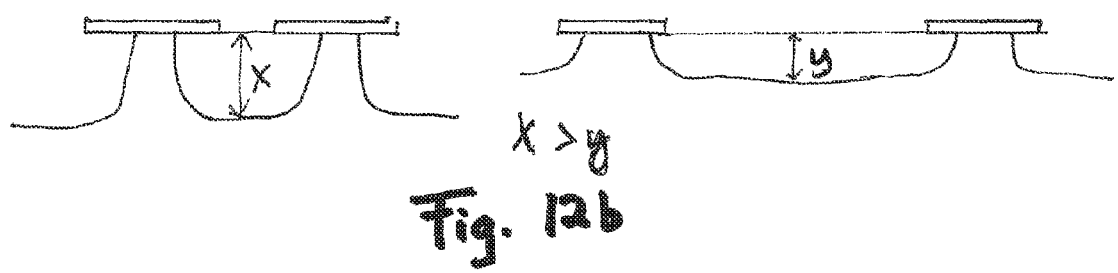

If needles are required having a fairly large spacing the above effect discussed in connection with FIG. 12 can be used. Namely, if a pattern is designed that in addition to defining the needles also defines additional sacrificial structures, e.g. in the form of thin walls surrounding the needles, the etching behaviour will resemble that of FIG. 12b. If the walls are defined to be thin enough, they will disappear when the etching of the needles is completed. This process is referred to as etch load compensation.

It is also possible to define "dummy" needles located outside the area where the actual needles of the device are located to obtain a similar effect. These "dummy" needles" can then be removed in connection with e.g. a sawing operation performed for other purposes. It is also possible to remove the "dummy" needles" with any other means or method that will not impair the desired structure.

Figure 36:
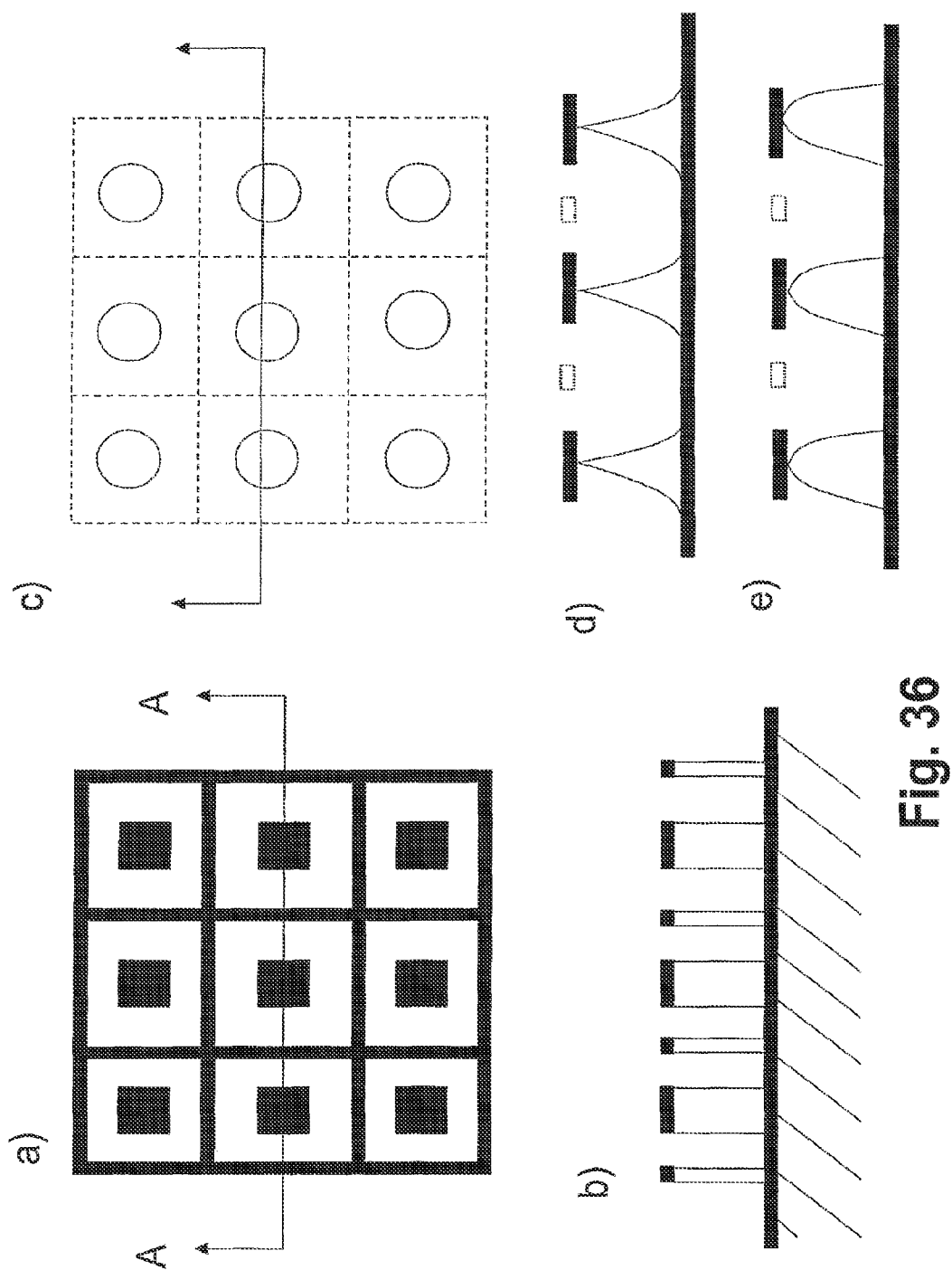
FIG. 36 illustrates etch load compensation.

In FIG. 36 this "etch load compensation" principle is illustrated. FIG. 36a shows a top view of a part of a wafer where blocks of silicon has been provided surrounded by thin walls by an anisotropic DRIE etch. FIG. 36b is a cross-section at A-A in FIG. 36a.

FIG. 36c illustrates in a top view of the result after isotropic etch, e.g. a wet HNA or a dry DRIE etch. FIG. 36d is a cross-section through FIG. 36c after one type of HNA etch yielding very pointed tips, and FIG. 36d is the result of another HNA etch yielding more blunt ended needles.

The present invention therefore relates to a novel process sequence for eliminating this "location effect", i.e. the invention provides a method that will generate uniformly high needles, and needles that are uniformly pointed, regardless of where on the wafer needles are located, or how close the individual masks are laid out on the wafer.

The novel method comprises only two etching steps, as opposed to the above mentioned iso-aniso-iso DRIE sequence, namely a first dry anisotropic etch followed by a wet isotropic etch (HNA etch; Hydrochloric acid:Nitric acid: Acetic acid).

Figure 13A:
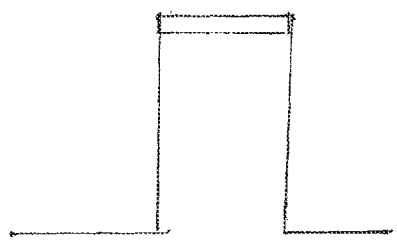
FIGS. 13a-b illustrate still another embodiment of the methods according to the invention.

Applying a dry anisotropic etch to a suitably patterned substrate (e.g. a pattern defining circular needles) will result in the structure shown in FIG. 13a, since the etch rate for the dry anisotropic etch is essentially the same in the vertical direction independent on pattern configuration or the location on the wafer of the individual pattern elements.

Figure 13B:
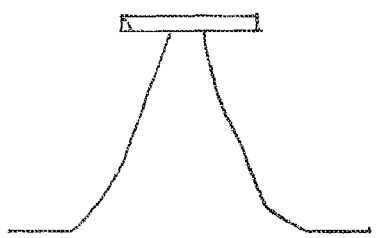

Next, the wet isotropic etch is applied to the structure obtained in FIG. 13a. The invention makes use of the fact that the wet isotropic is not 100% isotropic, but will actually etch slightly faster at the top of the "pillar" than at the bottom, resulting in the structure shown in FIG. 13b. The tip can then be sharpened in the same way as described in connection with FIG. 10e.

Finally, remaining mask material is stripped away.

Thus, there is provided a method for making uniformly high and preferably uniformly pointed needles, regardless of where on the wafer needles are located, or how close the individual masks are laid out on the wafer, comprising only two etching steps, namely a first dry anisotropic etch applied to a patterned substrate (e.g. a pattern defining circular needles), followed by a wet isotropic etch (e.g. HNA etch; Hydrochloric acid:Nitric acid:Acetic acid), which etches slightly faster at the top of the "pillar" than at the bottom. Preferably the tip is subsequently sharpened.

The method above can be equally well used for solid and hollow needles. In the latter case the methods described in connection with FIG. 6b (holes from the front side) and/or FIGS. 24a and 24e (holes from the backside) are usable.

Electrical Connections and Packaging

A still further aspect of the invention relates to the problem of achieving electrical connections between areas of a chip/wafer with various structures provided on the surface of said chip/wafer. The structures can be needles, or arrays of needles, made by any of the methods described above, or by any of the prior art methods. It is desirable to provide areas having suitable properties for packaging, soldering, "flip-chip" mounting, wire bonding etc.

Figure 14A:
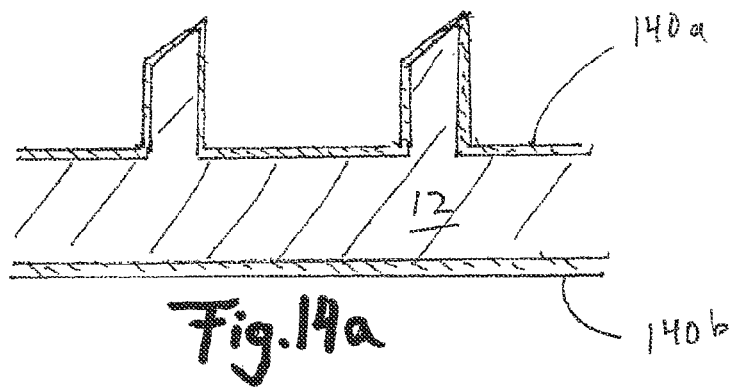
FIGS. 14a-c illustrates different approaches to make electrical connections between two sides of a wafer having needles thereon.

In a first embodiment, wherein the chip/wafer 12 itself is highly doped such that it exhibits a low resistance, a metallization layer/metal layer 140a, 140b is provided on the top and bottom surfaces, respectively, of a chip/wafer 12. Suitable methods are evaporation techniques, sputtering, plating, CVD and other methods available. In this case electrical connection is through the chip/wafer bulk, see FIG. 14a.

Such a metal layer can comprise (AlSiCu)+Ni+Au, a metal combination which is well suited for soldering or "flip-chip" mounting.

Also for applications wherein the needles are to be used as electrodes (EEG, ECG etc.) Ag and AgCl are suitable. AgCl is particularly useful and preferred due to its good biopotential signal pick-up capability, and is also compatible with current medical requirements.

For wire bonding Ti or TiW combined with Au, or Al(AlSiCu) are suitable metals.

The above described methods have the advantage that metal connections will not have to be glued directly onto the silicon by using conductive glue.

Figure 14B:
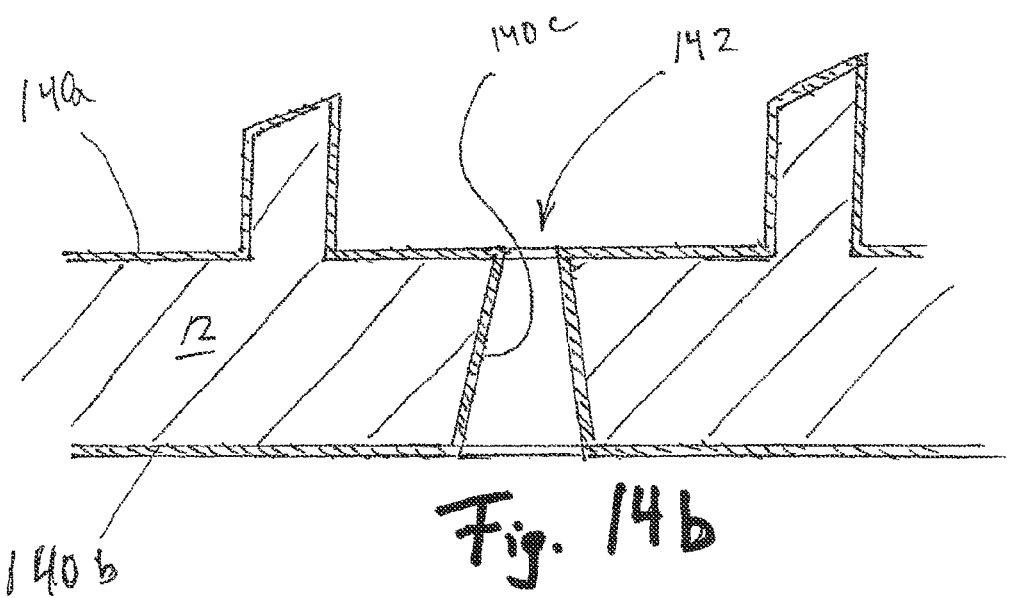

In an alternative embodiment, illustrated in FIG. 14b, which could be usable when the wafer material does not exhibit electrical conductivity, similar or the same metallizations as in the first embodiment can be used in combination with one or more through holes 142, the inner surfaces 140c of which also are metallized. Thereby connection between the top and bottom surfaces will occur through said holes.

The holes can be made by a number of different methods, e.g. wet etching, dry etching, drilling, laser, EDM etc.

Figure 14C:
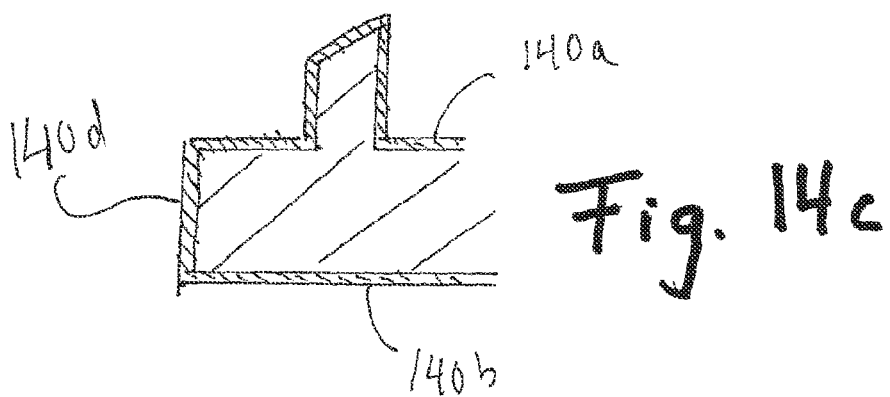

A variation of the second embodiment is to apply metallization layers to the edges 140d of the chip/wafer, such that connection is via the edges between top and bottom surfaces, see FIG. 14c. This in particular applicable whe SOI wafers have been used since there must be provided a "by-pass" connection to bridge the insulating material.

In a further embodiment of the above principle for establishing electrical connections between oppositely located surfaces, it can be desirable to isolate groups of structures (e.g. needles) on the top surface from each other while maintaining electrical connection between top and bottom.

Figure 15A:
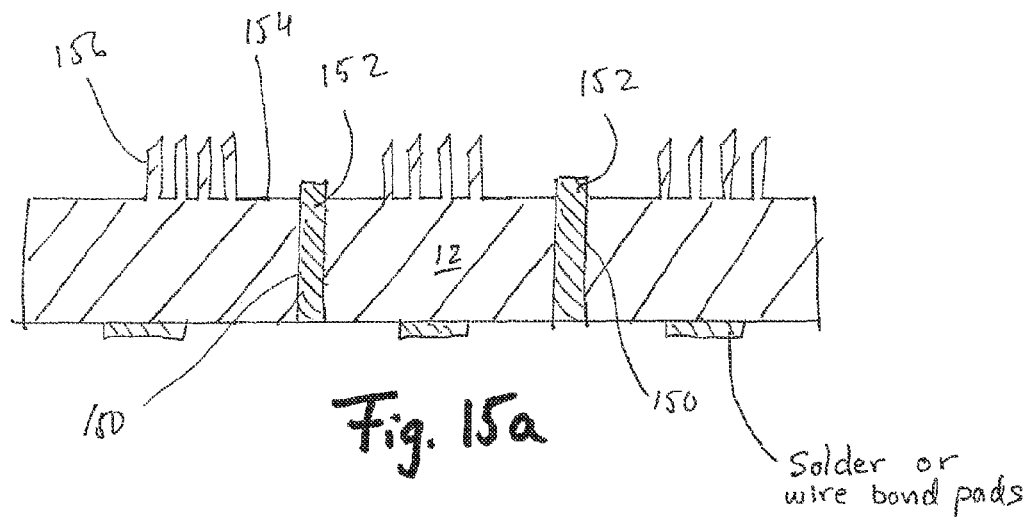
FIGS. 15a-c illustrates a number of methods of making arrays of needles in isolated groups on wafers and chips.

For this purpose a method invented by the applicants and disclosed in pending international patent application WO 04/084300 (corresponding to Swedish patent SE-526366) can be used. This method involves the provision of trenches 150 (i.e. deep recesses) extending all the way through the chip/wafer 12 from top to bottom surface, and filling said trenches with an insulating material 152, as illustrated in FIG. 15a. The trenches can be left as is, i.e. without filling in which case the air will function as the insulator. The disclosures of said application and patent are hereby included in their entirety by reference.

Thus, in a first variant of this method, a wafer having been provided with trenches as mentioned above, is used as the starting substrate for making the desired structured wafer. In one embodiment the chip/wafer is conductive, i.e. electrical connection is achieved through the bulk material. In this case, the electrical through connections would be made by the method(s) described in connection with FIG. 14a-c.

As can be seen in FIG. 15a, the insulating material 152 in the trenches 150 protrudes slightly above the base surface 154 from which the needles 156 protrude. This is because a pure silicon wafer has been used initially, and the trenches must than be etched to a desired depth with a small margin, such that it is ascertained that the discrete portions of the wafer carrying the needle structures actually will be isolated from each other.

Figure 15B:
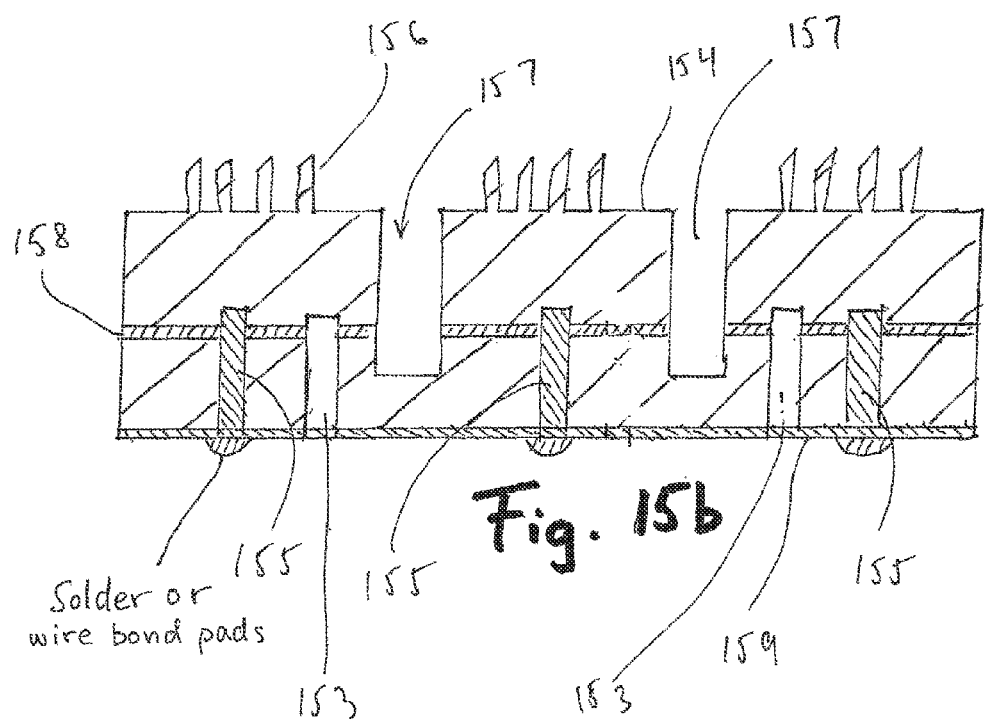

If an SOI wafer instead would be used initially when the trenches are made, this effect can be avoided. Namely, FIG. 15b illustrates another variant wherein an SOI wafer 14, comprising a buried insulating SiO$_2$ layer 158 is used initially for processing.

In this embodiment the methods according to the above mentioned patent (SE-526366) can be used to provide "vias" 155, i.e. electrical through-connections from the back-side, through the bottom silicon layer and through the insulator 158 into the front side material. However, it should be noted that vias made in any other way are usable for this embodiment, as long as they meet the requirements of the embodiment. Also, other methods can be used, such as the method disclosed in Swedish patent application SE-0600214-1 "Molten metal via" (Silex Microsystems). The vias are filled with a conductive material (i.e. metal, doped semiconductor etc.). However, the "vias" should only just about extend through the insulator material, suitably not more than a few µm, suitably 1-5 µm. Suitably the "vias" are made by pre-processing of the wafer, i.e. a wafer already having been provided with vias is used as a starting wafer.

After suitable processing to make the desired structures, such as micro-needle arrays on the front side of the SOI wafer, electrically isolated discrete portions of the wafer caryring array groups are made by providing recesses 157 in the front side base material that extend down to and/or through the insulator layer 158 in the SOI wafer. These recesses can be made by sawing, in which case the depth of the recesses should be sufficiently large to extend through the insulator. This is because the sawing process generates particulate material that could cause short-circuits between the array groups. Thus, a margin of about 25 µm down below the insulator layer 158 is required.

Alternatively, such insulating recesses can be made by etching, laser cutting or any other method that is capable of providing recesses of desired depths and widths. In the case of etching, the insulator layer could act as an etch stop in which case the recesses will only extend down to said layer.

In order to improve the insulating properties, and/or the strength of the structure as a whole, the recesses can be filled with insulating material, such as an oxide.

The back side of the finished wafer should be provided with a conductive layer 159, e.g. a metallization, such as the ones described above, i.e. a metal layer comprising (AlSiCu)+Ni+ Au for soldering or "flip-chip" mounting (currently it is common to use lead solder, but there is a strive to go away from lead. Instead AuSn or AgSn are possible materials), or for wire bonding Ti or TiW combined with Au, or Al(AlSiCu).

Furthermore, in order to separate the areas that are to be electrically insulated, one has to provide recesses 153 on the bottom-side that are similar to the recesses 157 on the top side. Thereby, sawing, etch or laser cutting can be used also for making the bottom-side recesses 153, care being taken to ascertain that the recess 153 extend at least up to the insulator layer 158 in the SOI wafer. If sawing is used to provide the recess, it should preferably be made so as to extend slightly into the silicon on the top side, as can be seen in FIG. 15b.

It should be pointed out and emphasized that the use of trenches for providing vias and/or insulating separation members, as described above, is advantageous in that it will become possible distribute groups or arrays of needles in an arbitrary manner. When trenches according to the above described methods (see the cited patent) are used for making the chips, the geometry will only be restricted by the limitations inherent in the patterning/etching processes that are available. For example it will become possible to manufacture round/circular chips. Round chips are particularly advantageous for applications with emitting tips. In the case where sawing is used to separate such groups, only rectangular shapes are possible.

Figure 15C:
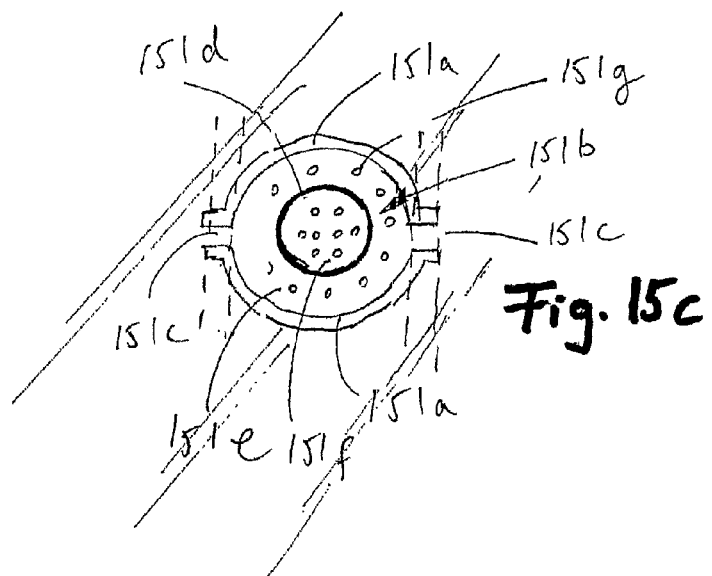

FIG. 15c illustrates an exemplary embodiment wherein a round chip having micro-needles is made.

It involves making two semi-circular trenches 151a defining a circular chip 151b. The semi-circular trenches are laid out such that they do not meet at two diametrically opposed positions. This lay-out will define a couple of beams 151c carrying the chip connecting it to the surrounding wafer material, thereby keeping it in place during processing. A second circular trench 151d is provided in the circular chip, and filled with an insulating material, thereby defining two concentric areas 151e and 151f, respectively, on the chip 151b which are electrically insulated from each other. Needles 151g can then be made on the chip according to a desired design (solid, hollow, electrically connected to the back-side or not etc.). Finally, the individual chips are released from the wafer by a sawing operation along indicated cutting lines (parallel broken lines in FIG. 15c defining a sawing recess).

The chips can be provided with metal on the back-side, for the purpose of enabling soldering, and if solder bumps are provided, the circular chips are ideal for flip-chip mounting.

A variant of the method, described above, wherein electrical contact is achieved by covering the edges of the chip/wafer with metal will now be described.

In a case where a needle array chip is to be attached to a circuit-board, it may not be suitable to have contact pads for connection to other parts of the circuit-board on the bottom-side of the chip. Also, it is important that the needles actually constitutes a protruding portion, located at a higher level than any surrounding structure. If not, the needles could simply not be used as intended, e.g. for penetration of the skin.

Figure 16:
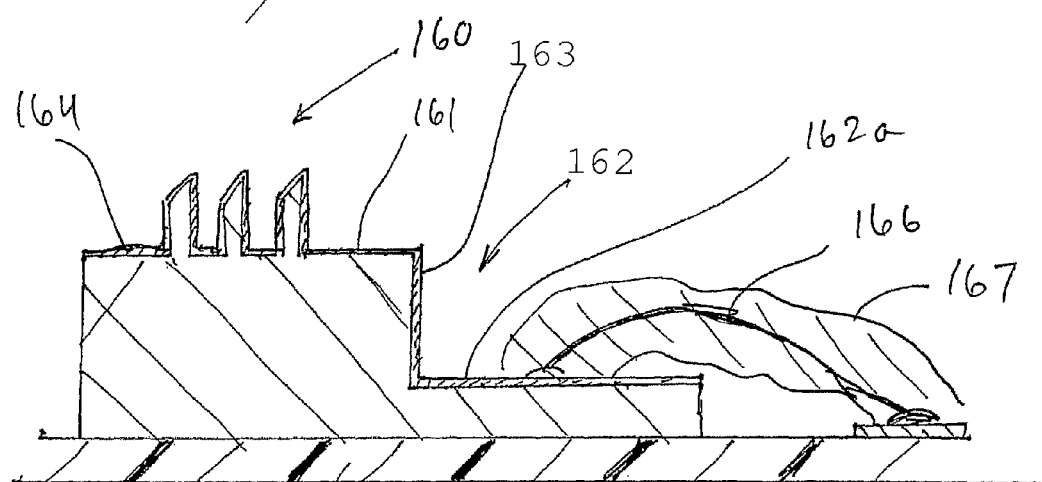
FIG. 16 shows in cross section wire bonding to a needle array device.

In order to make the structure shown in FIG. 16, which exemplifies the situation just described, the needle array 160 is made by any of the processes described herein previously. Then, instead of attaching connections at the bottom-side, the chip is provided with a stepped-down portion 162, as shown in FIG. 16, i.e. with a surface 162a located adjacent the area carrying the needle array 160 but at a lower level than the base surface 161 of the needle array 160. Such a step portion can easily be made by suitable processing, e.g. a lithographic patterning/etching process, or by sawing. This will not be described in detail, since the skilled man would immediately realize how to obtain it.

Once the stepped down portion 162 is provided, the entire upper surface of the chip, including the vertical wall 163 extending between the upper base surface 161 and the horizontal surface 162a of the stepped-down portion is metallized 164, such there will be electrical connection between the array of micro-needles 160 and the surface 162a of the stepped-down portion. Metallization is required for wire bonding, but it is possible to make electrical contact directly onto silicon by using conductive glue.

Then, the chip can be attached to a circuit-board 165, e.g. by gluing. Wires 166 can be attached to the chip at the stepped-down portion, and the wires are protected 167 by so called globbing, by providing "glob tops" (glob encapsulation).

This way, by providing points of attachment at a lower level than the needle array, the connecting wires will be "out of the way", and cannot interfere with the function of the needles.

Also, the chip can be placed with the needles pointing upwards during attachment of wires, which is advantageous in that there will be lees risk for damaging the needles during the mounting procedure in a manufacturing facility.

The above described methods constitute a collection of processes that can be applied in the manufacture of various devices. Below a couple of examples of such applications will be given, namely in the form of different embodiments of a chip carrying groups of micro needle arrays suitable for impedance measurements.

For this impedance measurement application it is necessary to create groups of needle arrays on one single chip, the arrays being electrically insulated from each other.

Figure 17A:
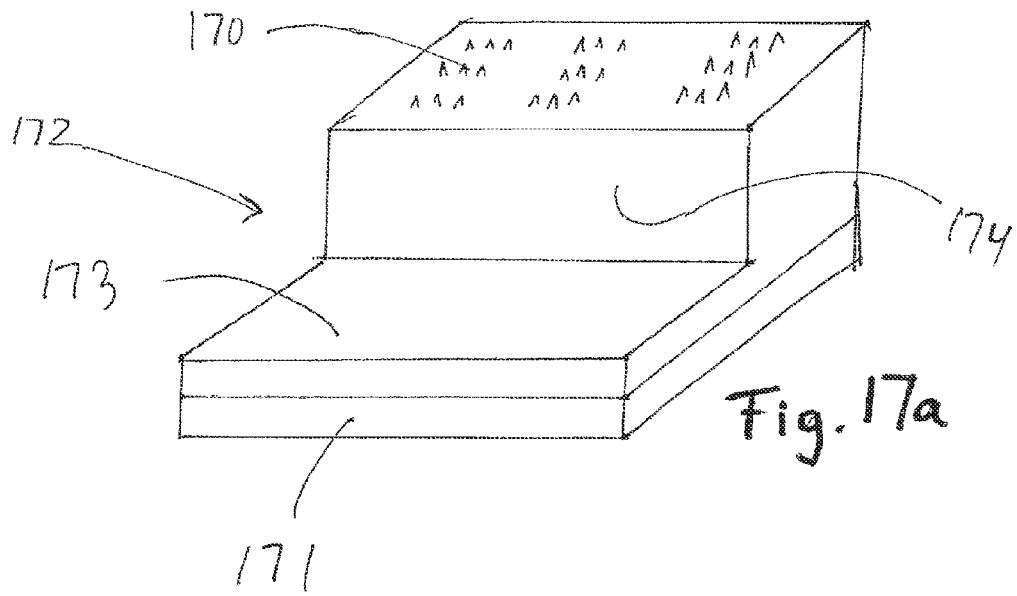
FIGS. 17a-b illustrates making a device for electrical impedance measurements.
Figure 17B:
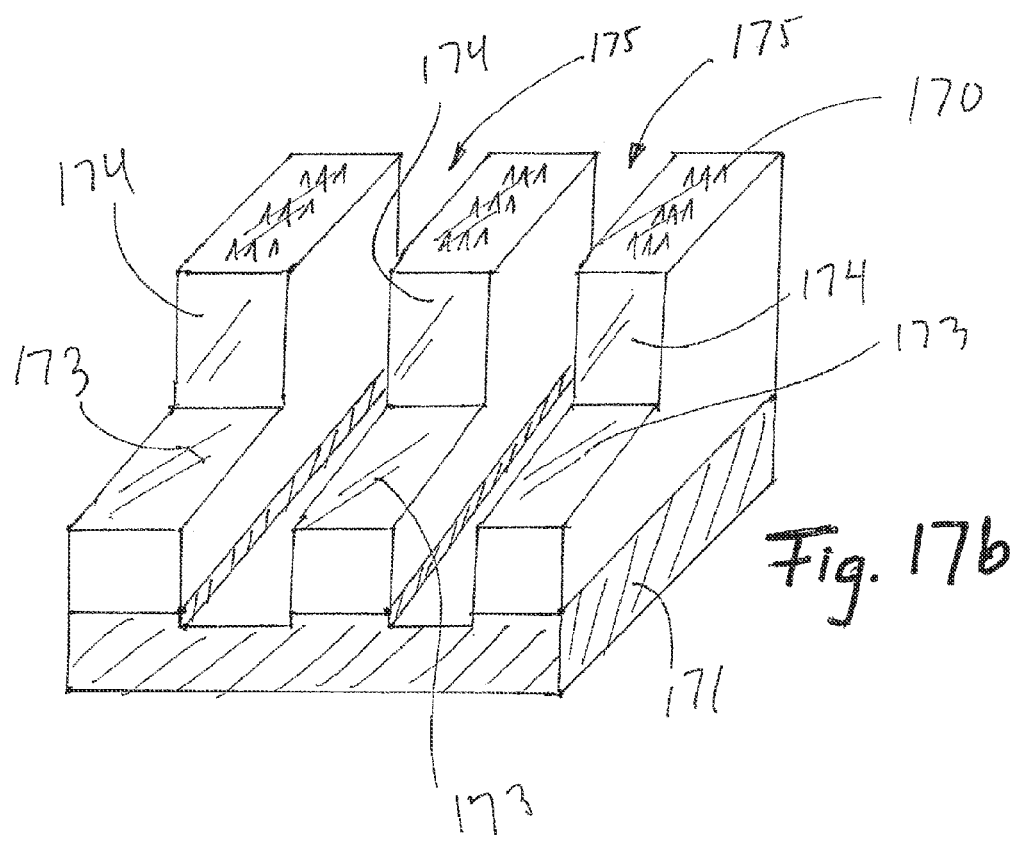

The process, being described with reference to FIGS. 17a-b starts with making needles laid out in suitable patterns on a wafer, employing any of the above described methods. Thus, both solid and hollow needles are possible. However, for pure impedance measurements solid needles are preferred. When the needles 170 have been made, the wafer is attached to a glass substrate/wafer, 171 suitably by anodic bonding. The glass wafer will provide an electrical insulator that separates the arrays electrically (see further below). It also functions as a carrier that exhibits the required strength. In order to provide for electrical connections to the individual groups of arrays, a stepped-down portion 172 is provided by sawing or by etching, as described in detail above. The "shelf" 173 thus made will form the base for the provision of wire bonding at a later stage in the processing.

The entire wafer is metallized and preferably care is taken to ascertain that also the vertical walls 174 of the stepped-down portion is metallized to provide good electrical connection between the needle base (upper surface) and the stepped-down portion forming the bonding area. This is however not strictly necessary if the silicon wafer itself is sufficiently conductive such that electrical connection between needles can be achieved through the wafer bulk material. However, if an SOI wafer is used a "by-pass" connection must be provided (see below, FIG. 19)

When the wafer is appropriately metallized, i.e. both the needles and the contact surfaces (stepped-down portion) are made sufficiently conductive, the groups of needle arrays on one individual chip are separated electrically from each other by sawing or laser cutting recesses 175 down through the silicon bulk material and slightly down into the glass bottom substrate. Thereby electrically insulated groups of needle arrays 170 are provided, see FIG. 17b.

Instead of using a pure silicon wafer, an SOI wafer can be used as a starting substrate, in which case there will be no need for bonding the silicon wafer to a glass wafer. Instead, the buried oxide layer 180 in the SOI wafer will provide the required electrical insulation between array groups 182, see FIG. 18.

The SOI wafer should in this embodiment have a device layer that is 150-200 μm thick, in order to enable the manufacture of needles of appropriate size, and a handle layer that is approximately 1000 μm thick, in order to provide the necessary mechanical strength.

The same procedure as in the previous embodiment is carried out, i.e. needles are made by any of the previously describe methods, a stepped-down portion 184 is provided by sawing or etching, and the entire wafer is metallized.

However, in this embodiment it is very important that the vertical wall 186 of the stepped-down portion 184 is appropriately coated with metal, since the electrical current will flow only through the metal coating. In particular of course it will be very important that the exposed part of the insulator layer 180 on the vertical wall 186 between device layer and handle layer is covered with metal, since otherwise there would be no electrical connection between the needles and the horizontal surface 188 of the stepped-down portion where wires are to be bonded. The array groups 182 are separated from each other by sawing or etching a recess 189, like in the previous embodiment. In this case it is only necessary that the recess be so deep as to have its lowest point below the metallization of the stepped-down horizontal surface 188.

One advantage of using an SOI wafer, as described above, is that the needles can be made with highly accurate heights, since the oxide layer of the SOI wafer will act as an efficient etch stop.

Figure 19:
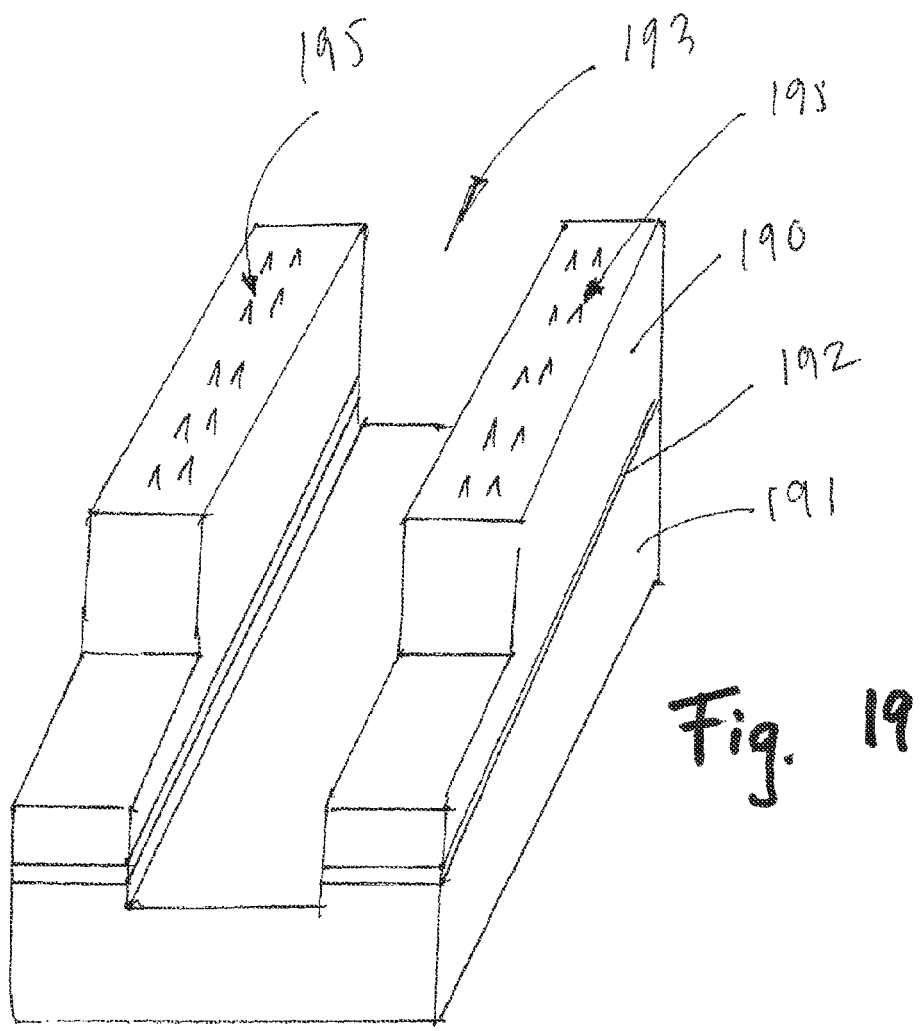
FIG. 19 shows another embodiment using an SOI wafer.

In a further embodiment an SOI wafer having a thick device layer 190 and a thin handle layer 191 can be used, see FIG. 19. The insulator layer 192 can be of the same thickness as for the previous embodiment. Thereby, essentially the same process steps as in the embodiment according to FIG. 18 will be carried out. However, in this case it will not be equally important to metallize the entire wafer. This is because when the separating recess 193 is made, the buried insulator layer 192 of the SOI wafer will provide the necessary insulation between the array groups 195, and the electrical current can be drawn through the bulk silicon material. Thus, there is no need for vertical wall metallization at the stepped-down portion.

In order to achieve better performance for impedance measurement devices (chips) according to the invention, adequate insulation must be provided between the groups of needles. To achieve this there must be a certain spacing between the groups (arrays) of needles on the chip, i.e. there must be a certain minimum area of insulating material between the arrays. The use of SOI wafers, which is beneficial from the point of view of enabling removal of the "grass" (residual extremely thin upstanding Si-structures on the wafer), also provides the desirable insulating surface. However, it is also required to provide electrical connection between needles and the silicon beneath the oxide surface, on which the needles are provide.

FIG. 25 and FIG. 26 illustrates two embodiments of the grouping of needles 252 on an impedance chip 250. In FIG. 25 the needles are provided on surface areas circular cylindrically enclosed by insulating oxide (so called vias 254), and in FIG. 26 the provision of insulating oxide structures 264 extending vertically through the wafer 260 and across the entire width so as to provide discrete blocks on which the needles 262 are provided.

Figure 27:
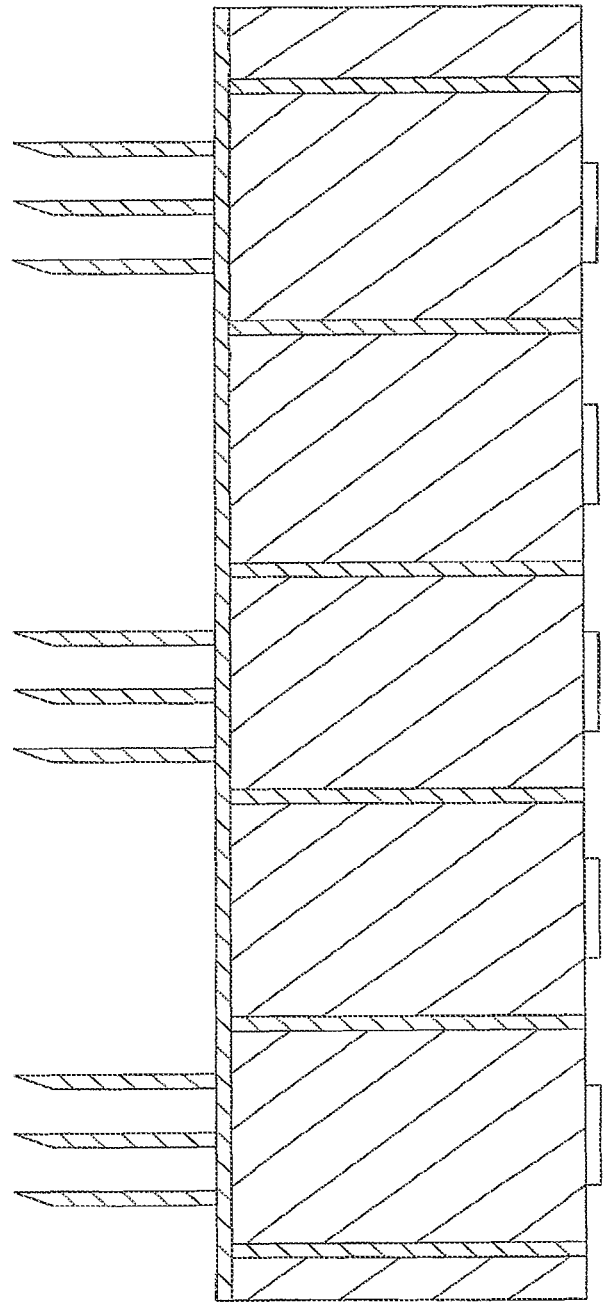
FIG. 27 shows a cross-section along the line A-A through the embodiments of an impedance measuring device according to the invention shown in FIGS. 25 and 26.

FIG. 27 shows a cross-section along A-A in FIGS. 25 and 26.

Figure 28:
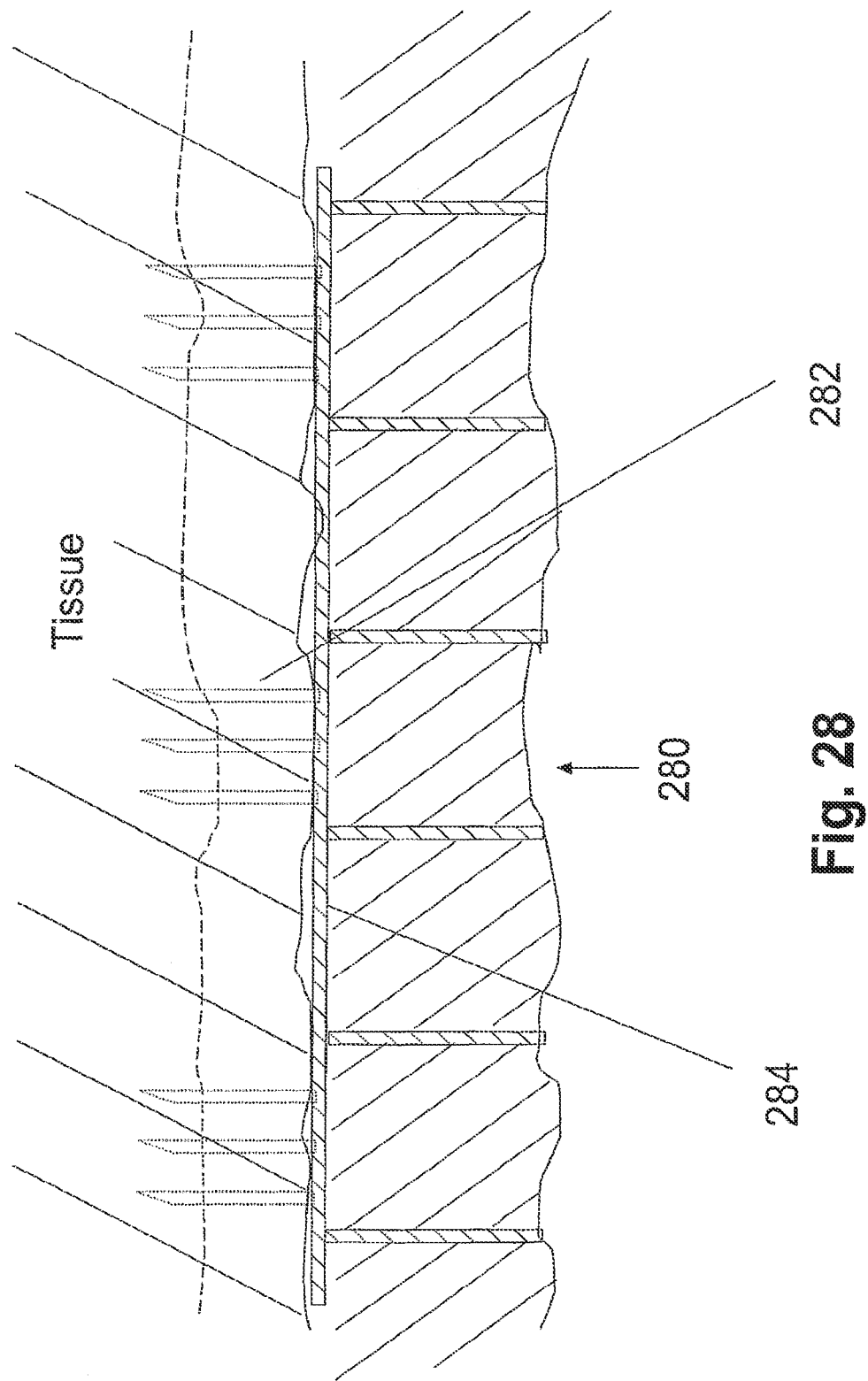
FIG. 28 illustrates schematically the penetration of a needle device into and through the skin.

The insulation between needle groups is also required in order to prevent the skin, in contact with which the entire chip 270 is brought, from short-circuiting the needles. This is illustrated in FIG. 28, where it is clearly seen that if the surface between the arrays of needles 272 were electrically conducting, a short-circuit would inevitably occur (in the figure there is an oxide layer 274 present).

Figure 30:
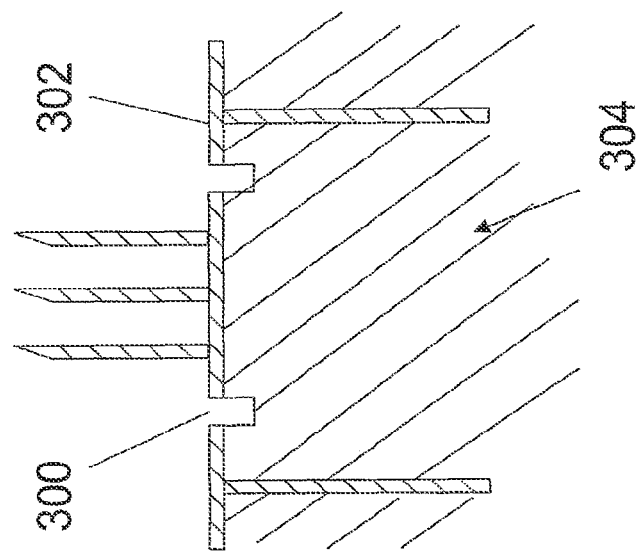
FIG. 30 is a cross-sectional view of the device in FIG. 29 after sawing.
Figure 29:
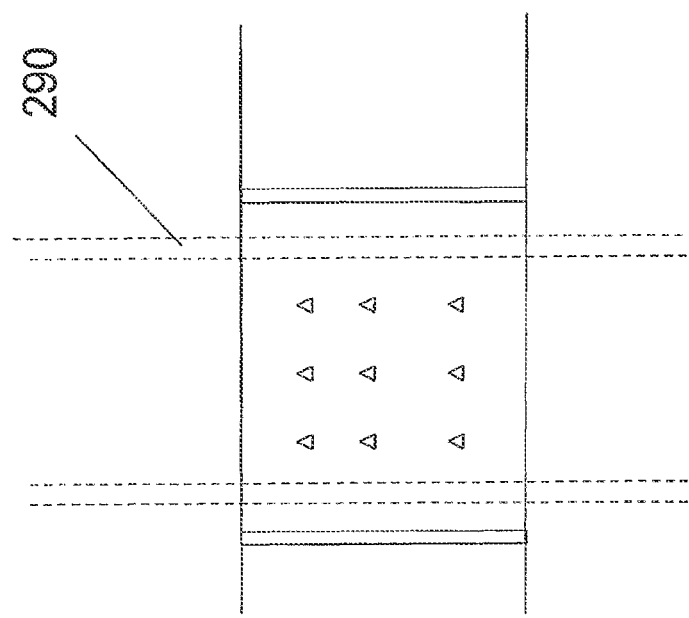
FIG. 29 illustrates removal of oxide by sawing.

On the other hand, as indicated above, one must provide electrical connection through the oxide and down into the silicon below the oxide surface. One simple way of achieving this is to saw grooves through the oxide (schematically shown in a top view in FIG. 29, wherein the saw grooves are indicated with dotted lines 290). FIG. 30 is a cross-section through a chip clearly showing grooves 300 extending down through the oxide 302 and into the wafer bulk silicon 304.

We now refer to FIG. 31. Having provided an opening in the insulating layer, a shadow mask 312 is provided over the chip 310, effectively exposing only the needles 314 and preferably only a part of the groove 316, and effectively shading those parts of the chip that still must be insulating 318. It is to be noted that this mask is a separate object placed over the structure to be processed. It is well known to the skilled man how to align the shadow mask pattern relative to the needle on the wafer by using e.g. wafer bond aligners. Alignment tolerances in the range of a few microns to a few tens of microns are easily achievable. I.e. it is not deposited as is the case with masks based on e.g. conventional photo-lithographic techniques using resists. Metal 319 is now deposited through the shadow mask, e.g. by sputtering or evaporation or any other suitable method. The metal will thereby cover the needles and the portion of the wafer that is exposed through the mask 312, forming a continuous layer over the exposed structures. The result will be an electrical connection between needles 314 and bulk wafer silicon 317, as shown schematically in FIG. 31.

The sawing method is only applicable to the embodiment according to FIG. 26 wherein the delimiting, vertical oxide walls inside the chip are straight, essentially "planar" structures.

For the embodiment of FIG. 25 with circular vias the sawing is if not impossible, at least extremely difficult to envisage, however blasting, laser cutting or drilling could be used. Thus, for this case a lithographic/etching procedure is preferable, illustrated in FIG. 32.

A resist 322 is applied to the wafer, taking great care to protect the needle tips with resist, and a suitable pattern is provided on the resist to open up holes or grooves in the resist through which an etchant can act through the mask and provide a slight over-etch down into the silicon. After removing the remaining resist, the result will resemble the structure shown in FIG. 30, however the groove can be made slightly shallower than the groove obtained by sawing or other non-photo-lithographic techniques.

An alternative to using the shadow mask is a procedure based on lithography and etching. For this embodiment a resist is applied to the wafer over its entire surface. Preferably the resist is applied by spraying, spinning, dip coating, laminating or roller coating, or electro-depositing. In this process it is very important that the tips of the needles be adequately protected by the resist. The resist is then patterned to provide the tracks for etching the grooves. An etch is applied through the resist pattern to remove the oxide and to provide an overetch down into the silicon.

The advantage with this approach is that the patterning can be made to fit essentially any geometry of the needles and vias, e.g the configuration shown in FIG. 26.

Figure 33:
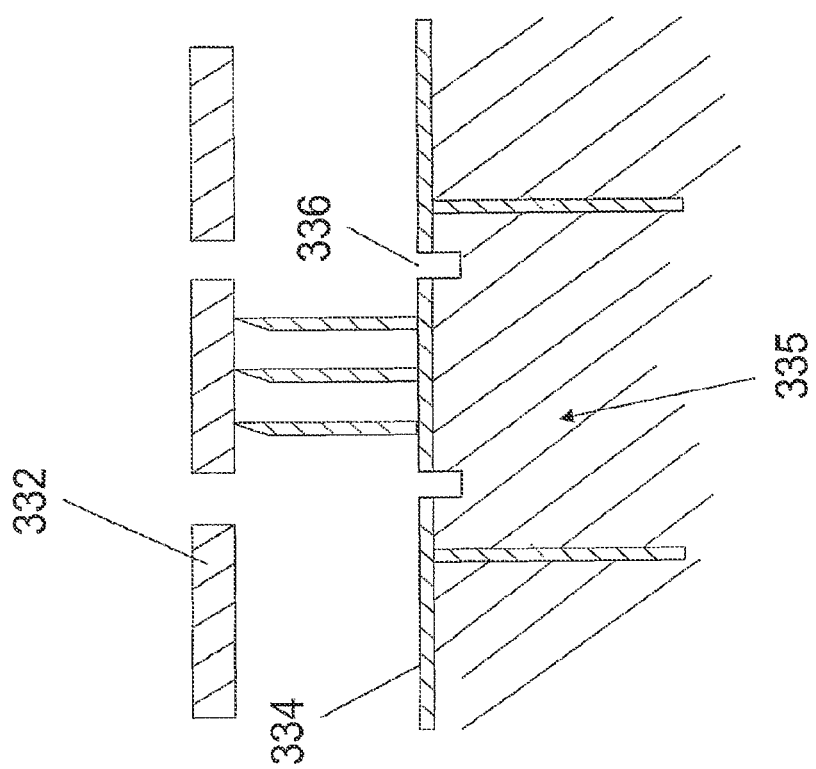
FIG. 33 illustrate a further alternative to sawing.

A further alternative embodiment for providing the necessary grooves is to provide a shadow mask as shown in FIG. 33, and to apply a suitable etch (e.g. dry reactive ion siliconoxide etch using high biasing) through the mask. The etch will remove oxide to expose the silicon and preferably slightly over-etch down into the silicon.

In a different approach to provide electrical connections between needles and silicon while at the same time insulate areas between arrays of needles is the following.

Figure 34:
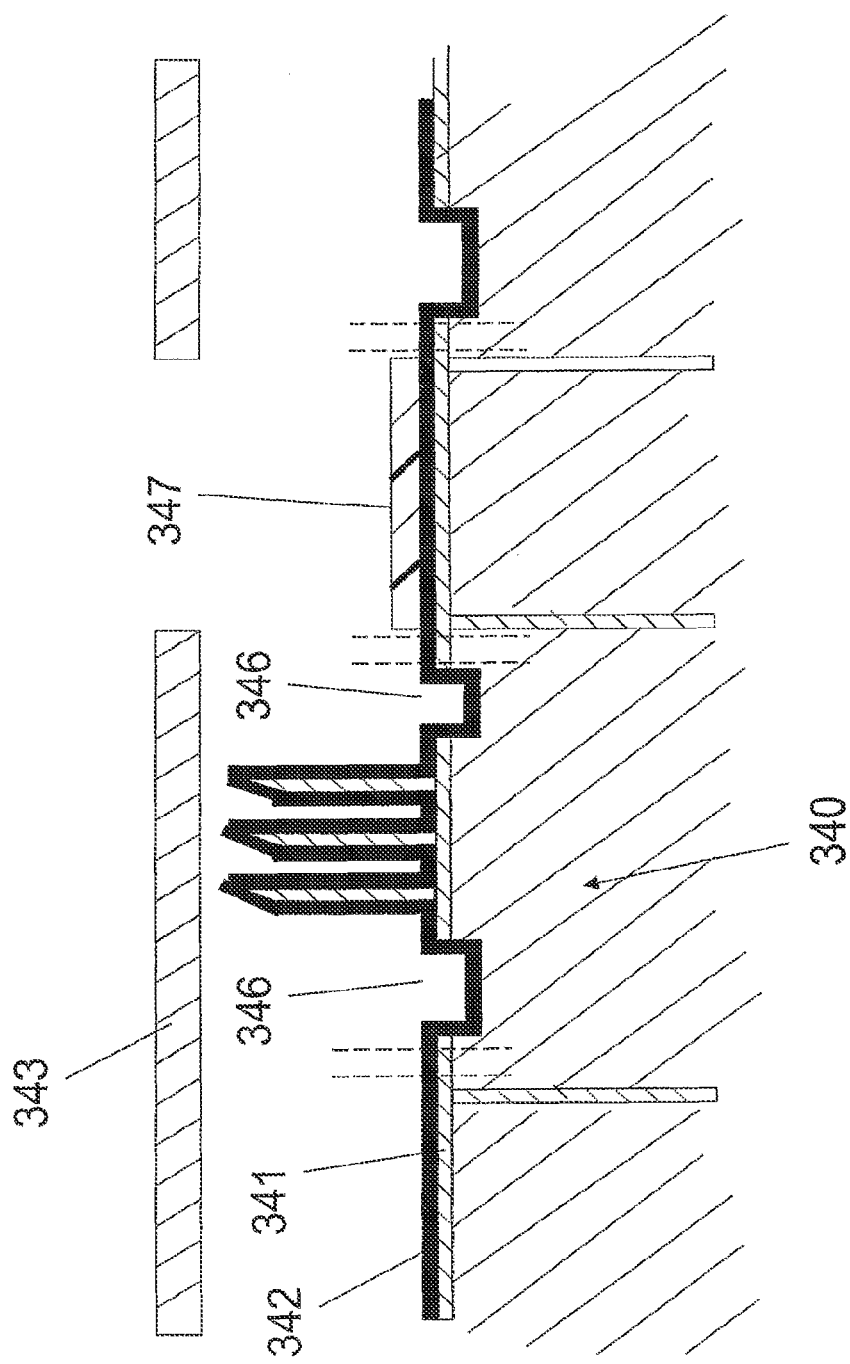
FIG. 34 illustrates provision of electrical connections and insulation of groups of needles by metallization by deposition through a shadow mask and deposition of insulator through shade-mask.

Referring to FIG. 34, the starting point for the procedure is a structure as shown in FIG. 30 or FIG. 32, i.e. a wafer where grooves have been made by sawing or etching. Thus, starting from a structure as indicated, first a layer of metal is deposited by suitable methods (e.g. sputtering, evaporation or similar methods). A shadow mask is positioned above the wafer so as to expose the areas between needle arrays where it is desirable to provide the insulator. Insulator (e.g. different silicon oxide, silicon nitride and similar compounds) is then deposited by sputtering, evaporation PECVD through the mask. In order to electrically insulate needle arrays from each other a sawing operation is performed at the locations indicated by dotted lines in FIG. 34. The groove obtained must extend through the oxide layer and into the silicon, whereby the electrical connection in the metal layer is disrupted.

Finally, in a still further variant for providing electrical connection between needles and silicon, a lift-off procedure is performed as follows.

Figure 35:
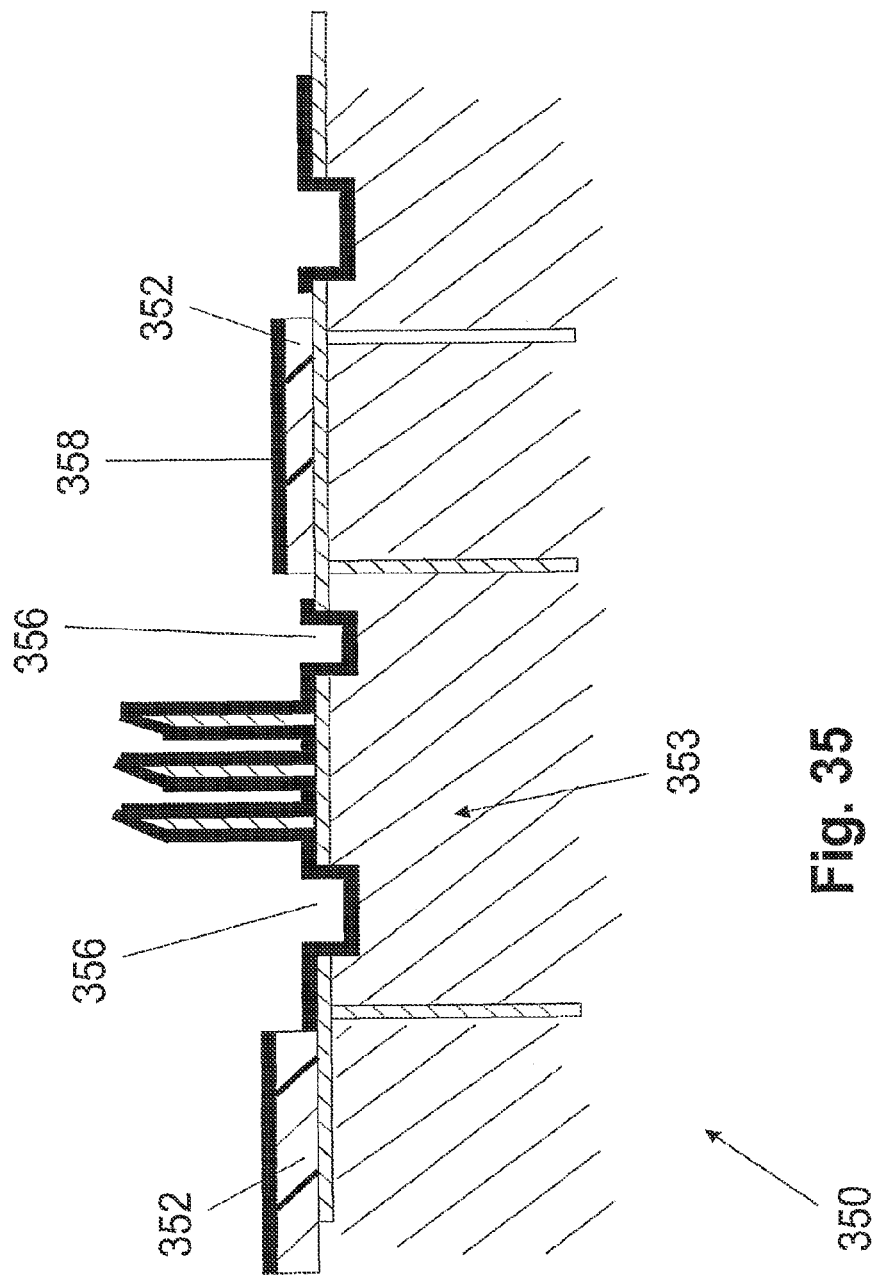
FIG. 35 illustrates a similar procedure as in FIG. 34 but using a lift-off method for provision of insulation.

The same starting substrate as in the method described above with reference to FIG. 34 is used. Referring to FIG. 35, first a resist is applied to the wafer, e.g. by spinning. A standard lithographic procedure is performed to pattern the resist for defining the insulating areas between the needle arrays, i.e. the resist is removed on the areas where the needles are located. Then a metal layer is deposited over the entire wafer. It should be noted that the resist, having a finite thickness, will exhibit vertical walls at the edges of the resist layers. During the metal deposition no metal will be deposited on these vertical walls. Finally, a lift-off is performed, i.e. the wafer is exposed to a suitable solvent. To dissolve the resist, whereby the metal deposited on top of the resist will also be removed, whereas the metal deposited on the needles and adjacent portions of the wafer will be left. Thus, electrical connection between the needles and the silicon in the grooves.

As already indicated previously in this specification, hollow needles made according to the present invention are very well suited for the delivery of fluids, such as drugs, to patients through the skin. In order to enable such delivery, of course the fluid has to be transported from some reservoir, external to the micro needle device, and fed into the chip for subsequent delivery through the plurality of needles of an array.

Figure 20:
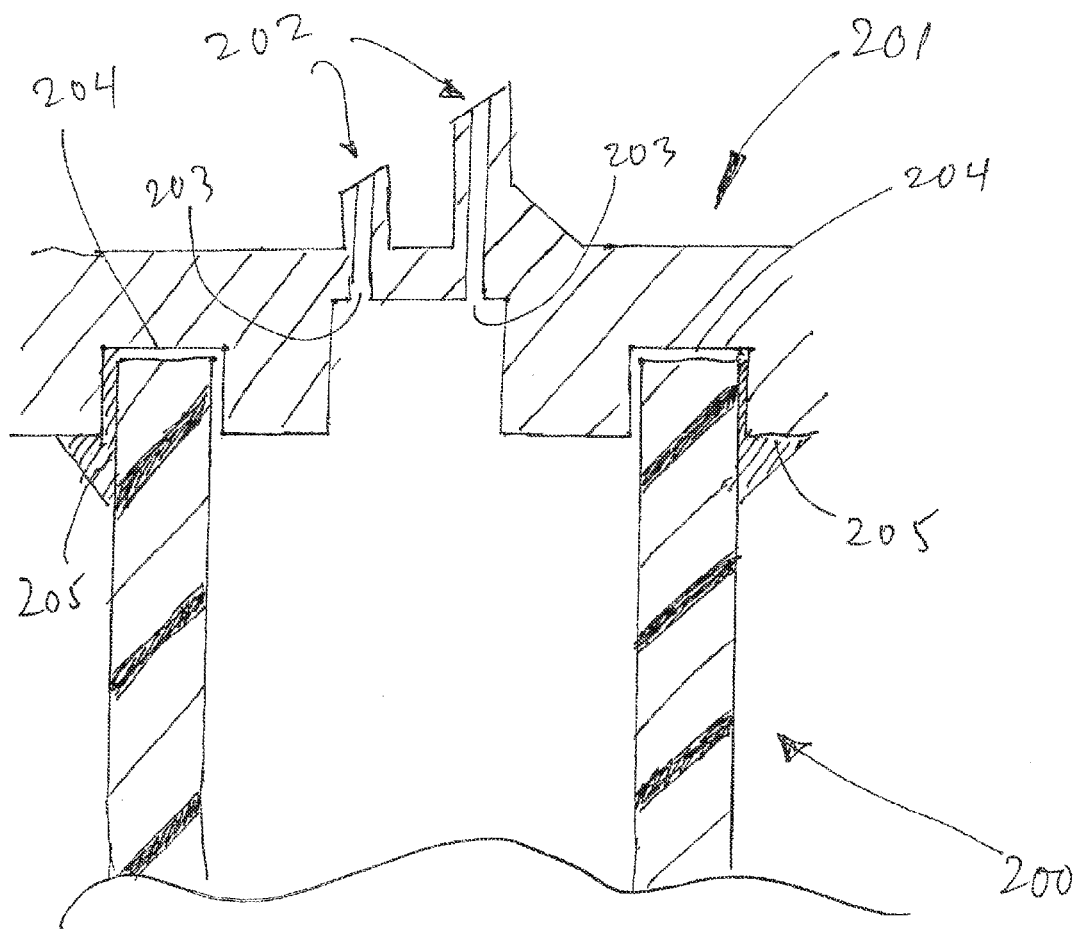
FIG. 20 shows connection of a tube for liquid delivery to a device having an array of hollow needles for medical use.

In FIG. 20 there is shown an example of how such a connection can be designed in accordance with a further aspect of the invention.

Thus, fluids are normally delivered through flexible tubing 200 having diameters in the mm scale, and thus have to be connected to a chip 201 with connectors of the same dimensions. A solution to this is to provide a chip having a plurality of hollow needles 202, wherein the inlets 203 to each needle 202 on the back side of the chip 201, are enclosed by a circular recess 204 having a width corresponding to the thickness of the tubing 200 material, thus having an inner and outer diameter corresponding to the inner and outer diameter, respectively of the tubing 200. The tubing is inserted into said recess 204, preferably in a relatively tight fit, but secured in place suitably by gluing 205.

In a still further aspect, the invention relates to a method of making protruding members, e.g. needles, having side openings, and closed tips. Such needles and manufacturing thereof are disclosed in WO 2003/015860 (Stemme et al).

Figure 21:
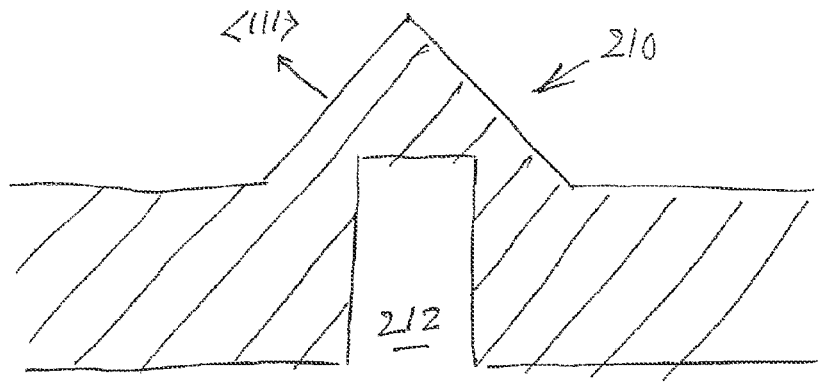
FIG. 21 is a cross section through a wafer on whcih a pyramidal structure has been made in accordance with the invention.

The present process comprises as an initial step the provision of an inclined surface, using any of the methods described previously herein. Thus, as shown in FIG. 21, a pyramid-like structure 210 having surfaces exposing the <111> planes is made by KOH etching after appropriate masking. Of course the structure can be other than pyramidal; e.g. if an elongated structure is made it will resemble a ridge rather than a pyramid.

Then a hole 212 is made from the backside, matched to the pyramid/ridge such that the hole is located essentially centred below the apex of the ridge. This approach will give a structure having side openings in all four directions, see FIG. 24a.

However, from a strength point of view it may be advantageous to make only one side opening. To achieve this it would be necessary to misalign the hole from the backside, i.e. giving it an off-set in one direction, see FIG. 24e.

At this stage in the process a double lithography (FIGS. 22-23) is performed to make two masks, one on top of the other. A first mask is made by oxidation to provide an oxide layer that subsequently is appropriately patterned, to provide a pattern of first masks, and then a second mask can be made by depositing a second oxide on top of the first, or by depositing resist on top of the first oxide layer, in a suitable pattern.

Figure 22A:
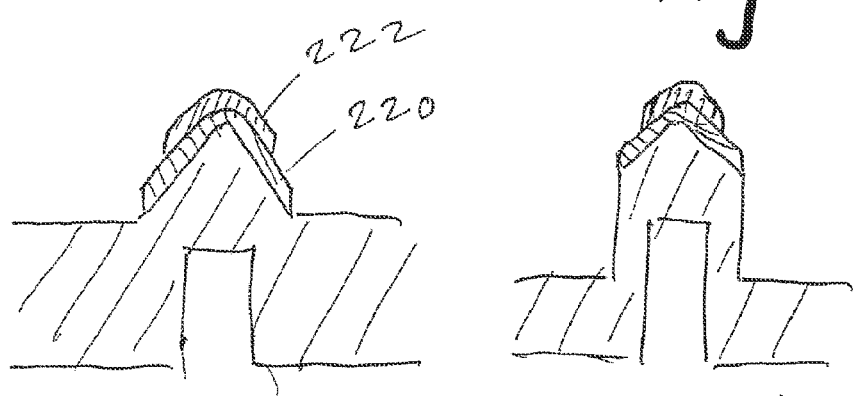
FIGS. 22a-b and 23a-b shows masking structures for different embodiments for making needles with side openings.

In the first case the cross-section through the mask structure will be as shown in FIG. 22a, i.e. the first mask (oxide) 220 is larger than the second mask (oxide) 222, and thus the first mask will define the base geometry of the protrusion (needle), whereas the second mask will define the final geometry of the side-opened needles.

Figure 23A:
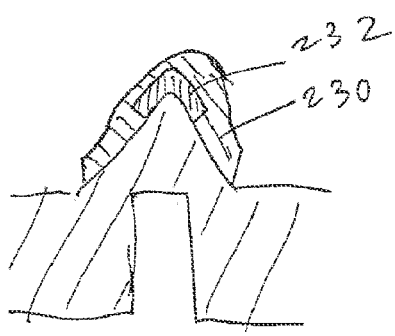

In the second case the cross-section through the wafer and mask structure will be as shown in FIG. 23a, i.e. the second mask 230 (resist) is larger than the first mask (oxide) 232 and covers it, i.e. the second mask will define the base geometry of the protrusion (needle), and the first mask will define the final geometry of the side-opened needles.

In both cases, the smaller masks will cover an area in the horizontal plane that is slightly smaller than the area of the circular hole made from the bottom of the substrate, i.e. at least one segment of the circumference of the hole will not be covered by the mask. If several side openings are desirable, the mask must leave a plurality of segments uncovered by the mask, see FIG. 24c.

Suitably however, the hole from the back side will be given a shape in cross-section that is not circular (see FIG. 24d). A cross-shaped section will enable stronger structures between the openings and connecting the base and the top of each needle. Of course any other geometry can be used as long as the desired openings are created in the final structure.

Figure 22B:
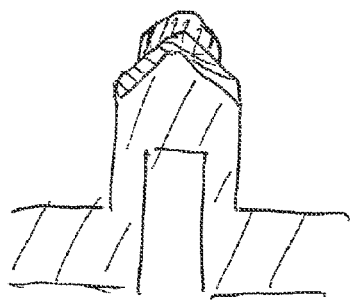
Figure 23B:
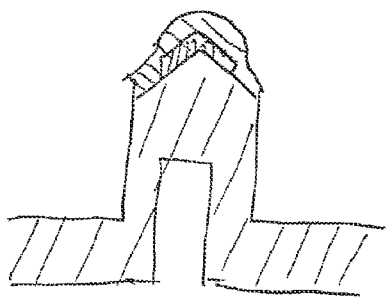

Thus, when both masks have been provided to make a double patterned substrate, a DRIE etch is applied to the double patterned substrate, which will remove material selectively in the vertical direction, and independently of crystal plane orientation, for making the "pillars" of the needles, resulting in the structures shown in FIGS. 22b and 23b.

Thereafter two different processes must be employed for the two alternatives. In the first alternative with both masks consisting of oxide, a "blank etch" is performed, i.e. oxide is removed down to the substrate. Since the second mask is on top of the first mask, thereby increasing the oxide layer to the double thickness, a portion of the first mask located under the second mask will remain, thereby defining a small mask.

For the second alternative, the resist is simply dissolved away using an appropriate solvent, thereby exposing the first mask defining a mask with the same geometry as the mask in the first alternative. These two alternatives will yield exactly the same end structure, provided of course the patterns are identical.

Figure 24B:
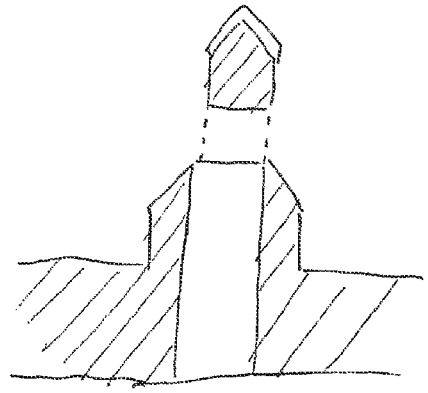
FIGS. 24a-d shows various aspects of the process for making needles having side openings.
Figure 24C:
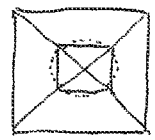
Figure 24D:
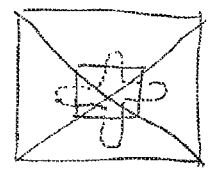

Again a DRIE is applied which will remove material in the vertical direction down to a selected distance, as shown in FIG. 24b, where about half of the pillar height is removed in this step. This will open up side openings, by virtue of the fact that the circumference of the circular hole will extend beyond the limits of the area defined by the small mask. In FIGS. 24c and 24d this relationship is schematically illustrated in a top view where the circular hole is indicated with broken lines and the small mask is shown to cover a portion of the pyramid only.

Figure 24A:
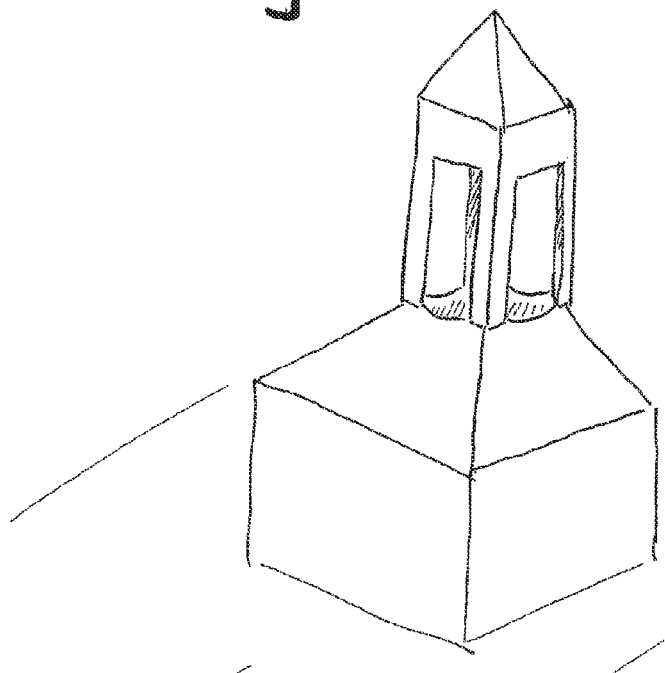
Figure 24E:
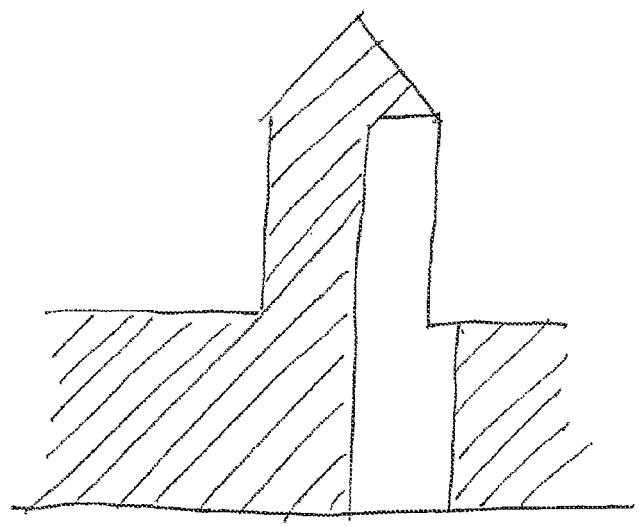
FIG. 24e shows a needle with a side opening in cross section.

When the side holes have been successfully made, the mask is removed and the tip of the needle is sharpened by oxidation. FIG. 24a shows a final structure in perspective.

There are numerous possible variations in the lay-out of mask patterns in order to vary the geometry of the needles.

The methods and devices (needles, needle arrays etc.) disclosed herein can be subject to numerous variations and applications. In particular for medical applications one could mention specifically:

drug delivery (e.g. "smart plasters", spray tips)

biopotential measurements (EKG, EEG, EMG etc.)

sampling of body fluids spray tips for nano-electrospray ionization mass spectrometry In the non-medical field the following applications can be mentioned as examples:

AFM/STM tips, field emission tips, tunnelling tips, probe card tips

"ink jet" or "out-of-plane" spray tips, etc.

We claim:

1. A method of making devices for electrical measurements, each device comprising a plurality of micro-electrodes in the form of micro-needles protruding vertically from a substrate, the method comprising the steps of:
 providing a substrate having a first side and a second side opposite the first side, and electrical connections between areas on the substrate located on the first side and second side of the substrate, said connections being electrically insulated from each other by vertical insulating trenches extending through the substrate; and
 making said micro-electrodes in the form of micro-needles on the substrate, wherein the micro-needles are made using a silicon on insulator (SOI) wafer with a silicon layer and a buried oxide layer whereby the micro-needles are provided on the buried oxide layer of the SOI wafer, and wherein the micro-needles are made in groups on areas located on the first side of the substrate;
 providing electrical insulation between said areas such that the groups of micro-electrodes are electrically insulated from each other, by forming a recess in the substrate through the buried oxide layer and into the silicon layer of the SOI wafer in a region between the micro-needles and the vertical insulating trenches;
 placing a shadow mask over the SOI wafer such that the micro-needles and preferably only a part of the recess are exposed through the shadow mask; and
 applying a metal coating through the shadow mask by sputtering or evaporation such that only the micro-needles and a part of the recess are covered by a continuous layer of said metal coating.

2. The method as claimed in claim 1, further comprising providing said vertical insulating trenches by placing a second shadow mask over the SOI wafer, said second shadow mask defining said vertical insulating trenches and applying a dry reactive ion etch with high bias through the second shadow mask.

3. The method as claimed in claim 1, wherein said electrical connections are defined by said vertical insulating trenches, each having a cylindrical form, extending through the substrate.

4. The method as claimed in claim 1, wherein said electrical connections are defined by two vertical insulating trenches, one from the first side and one from the second side and extending not all the way through but together electrically insulating said electrical connections from each other.

5. The method as claimed in claim 1, wherein the substrate is cut up to provide individual chips comprising two or more groups of micro-needles, said groups being electrically insulated from each other.

6. The method as claimed in claim 1, wherein the substrate is cut up to provide individual chips comprising single groups of micro-needles.

* * * * *